(12) United States Patent
Yamamoto et al.

(10) Patent No.: US 11,782,298 B2
(45) Date of Patent: Oct. 10, 2023

(54) ILLUMINATING DEVICE, IMAGING SYSTEM, ENDOSCOPE SYSTEM INCLUDING THE IMAGING SYSTEM, AND MICROSCOPE SYSTEM INCLUDING THE IMAGING SYSTEM

(71) Applicant: OLYMPUS CORPORATION, Tokyo (JP)

(72) Inventors: Eiji Yamamoto, Musashimurayama (JP); Bakusui Daidoji, Hachioji (JP); Yasuo Sasaki, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 884 days.

(21) Appl. No.: 16/687,787

(22) Filed: Nov. 19, 2019

(65) Prior Publication Data
US 2020/0081263 A1 Mar. 12, 2020

Related U.S. Application Data

(63) Continuation of application No. PCT/JP2017/018895, filed on May 19, 2017.

(51) Int. Cl.
*G02B 27/48* (2006.01)
*G02B 21/06* (2006.01)
(Continued)

(52) U.S. Cl.
CPC .......... *G02F 1/035* (2013.01); *A61B 1/00045* (2013.01); *A61B 1/063* (2013.01);
(Continued)

(58) Field of Classification Search
CPC ...... G02B 21/06; G02B 21/36; G02B 21/365; G02B 27/42; G02B 27/48; G02B 27/0933; G02B 27/1033; G02B 23/2469; G02B 23/2453; G02B 6/4292; G02B 6/4296; G02B 1/035; G02B 1/125; G02F 1/035;
(Continued)

(56) References Cited

U.S. PATENT DOCUMENTS

| 2010/0268034 A1* | 10/2010 | Krattiger | A61B 1/00165 600/178 |
| 2012/0249918 A1* | 10/2012 | Yasui | G02B 27/48 349/61 |
| 2016/0242626 A1* | 8/2016 | Daidoji | A61B 5/0066 |

FOREIGN PATENT DOCUMENTS

| CN | 105705074 A | 6/2016 |
| CN | 106384935 A | 2/2017 |

(Continued)

OTHER PUBLICATIONS

International Search Report dated Aug. 8, 2017 issued in PCT/JP2017/018895.
(Continued)

*Primary Examiner* — Jie Lei
(74) *Attorney, Agent, or Firm* — Scully, Scott, Murphy & Presser, P.C.

(57) ABSTRACT

An illuminating device includes an illumination light generator configured to generate illumination pulses of coherent light, and a speckle modulator configured to modulate speckle caused by the coherent light. The illumination pulse generator repeatedly generates a single illumination pulse group including a plurality of illumination pulses as a repetitive illumination pulse group.

20 Claims, 24 Drawing Sheets

(51) Int. Cl.
*G02B 21/36* (2006.01)
*G02F 1/035* (2006.01)
*G02F 1/125* (2006.01)
*A61B 1/06* (2006.01)
*A61B 1/07* (2006.01)
*A61B 1/04* (2006.01)
*A61B 1/00* (2006.01)

(52) U.S. Cl.
CPC .............. *A61B 1/0655* (2022.02); *A61B 1/07* (2013.01); *G02B 21/06* (2013.01); *G02B 21/361* (2013.01); *G02B 21/365* (2013.01); *G02B 27/48* (2013.01); *G02F 1/125* (2013.01); *A61B 1/00009* (2013.01)

(58) Field of Classification Search
CPC ....... G02F 1/125; A61B 1/063; A61B 1/0655; A61B 1/00045; A61B 10/07; A61B 1/00009; A61B 1/00165; A61B 1/00128
USPC ........ 359/385, 599, 558, 619, 250; 362/553, 362/559, 355
See application file for complete search history.

(56) References Cited

FOREIGN PATENT DOCUMENTS

| | | |
|---|---|---|
| JP | 2003-156698 A | 5/2003 |
| JP | 2013-048792 A | 3/2013 |
| JP | 2013-195506 A | 9/2013 |
| JP | 2014-239088 A | 12/2014 |

OTHER PUBLICATIONS

English translation of International Preliminary Report on Patentability dated Nov. 28, 2019, together with the Written Opinion received in related International Application No. PCT/JP2017/018895.

Chinese Office Action dated Apr. 29, 2021 received in 201780090987.2.

* cited by examiner

Position on imaging surface

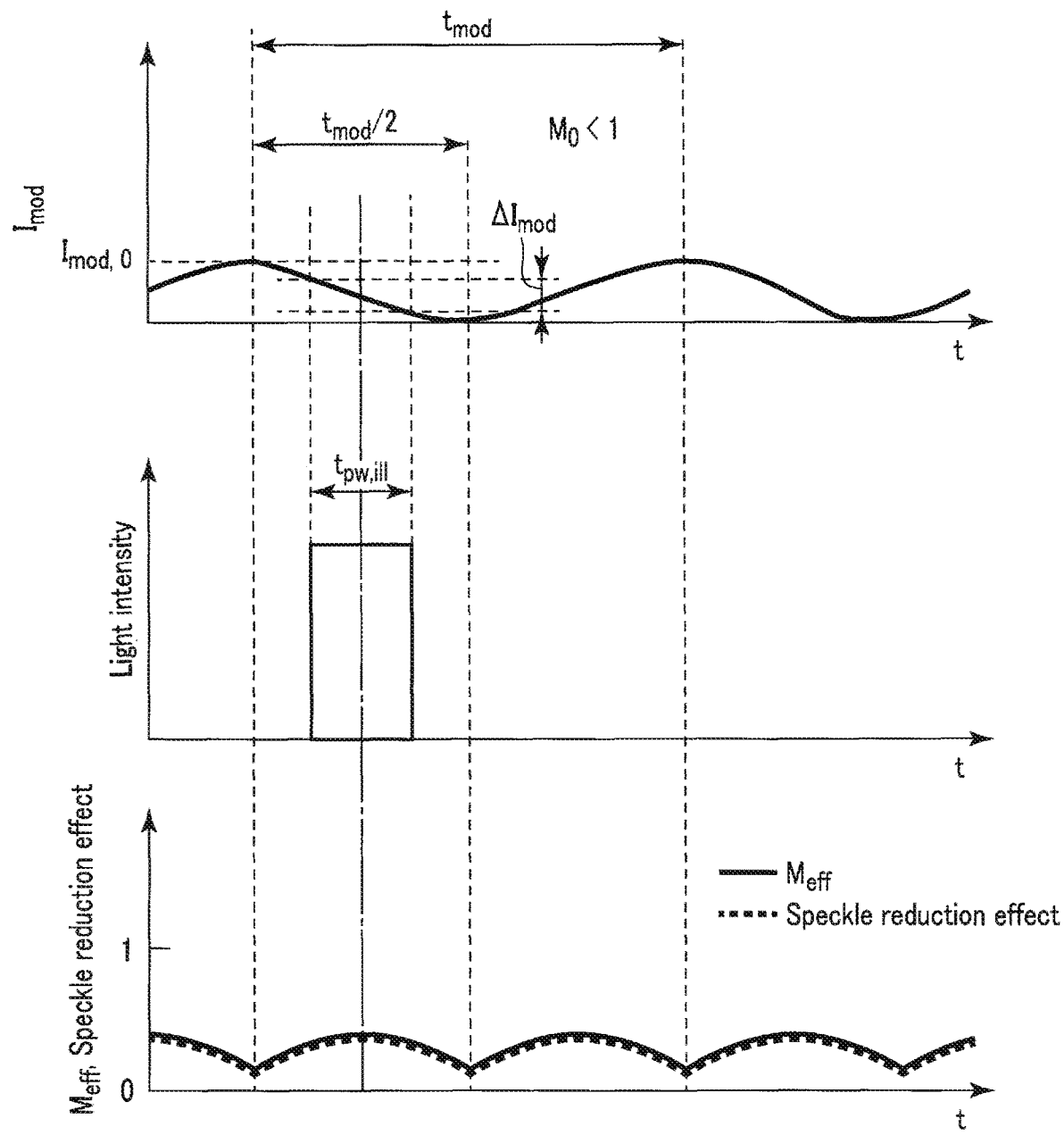
FIG. 3A1

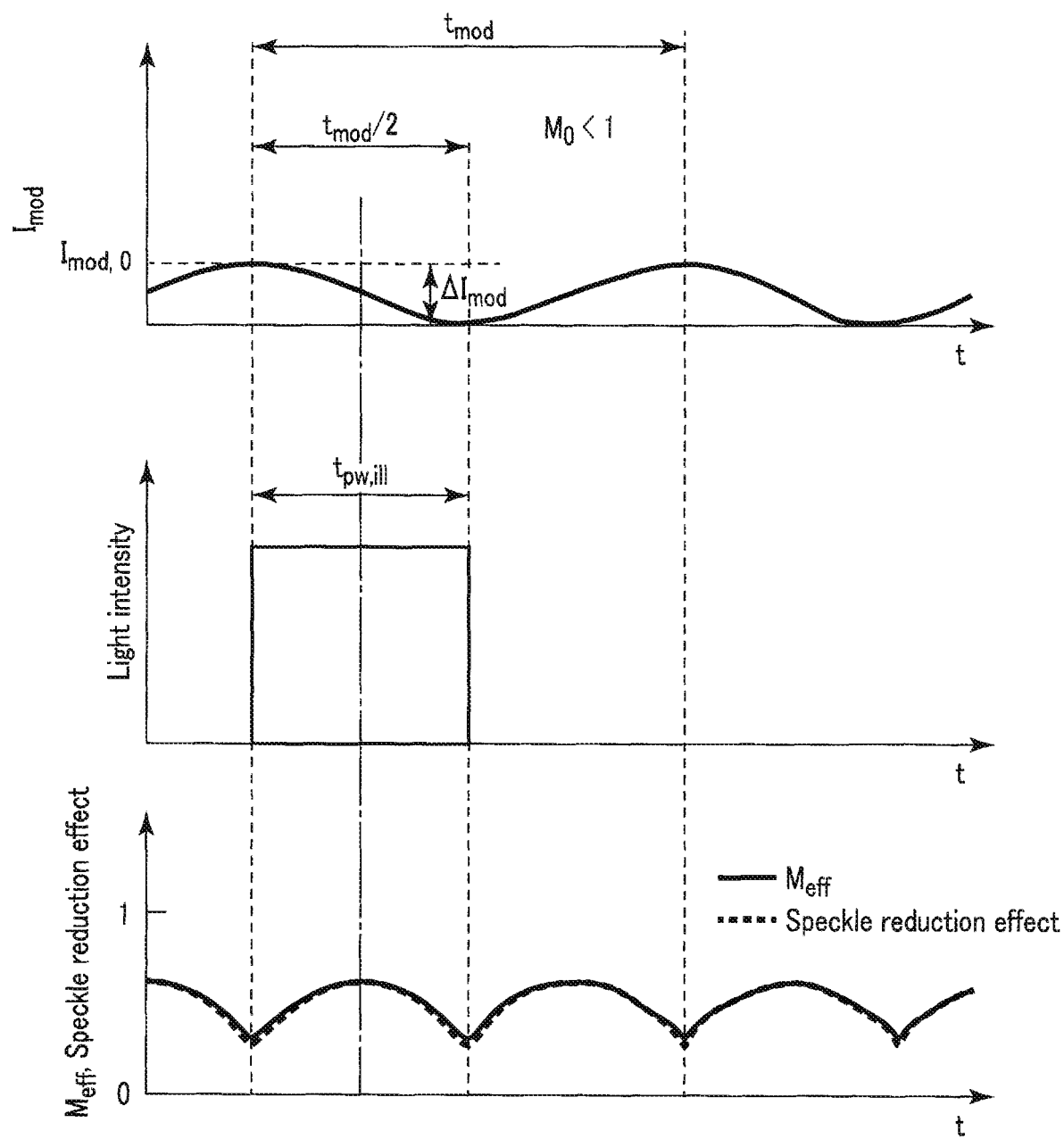
FIG. 3A2

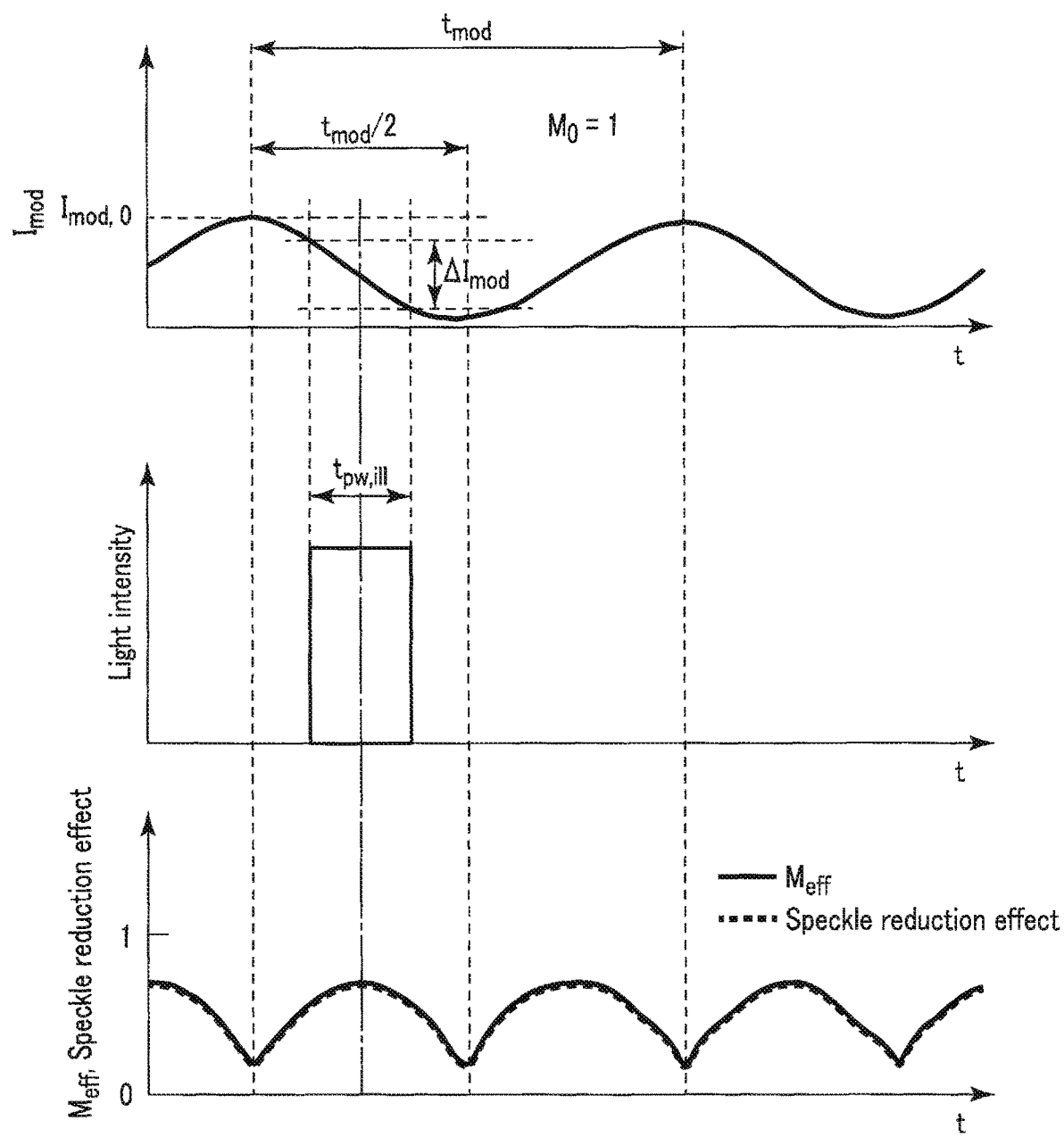
FIG. 3B1

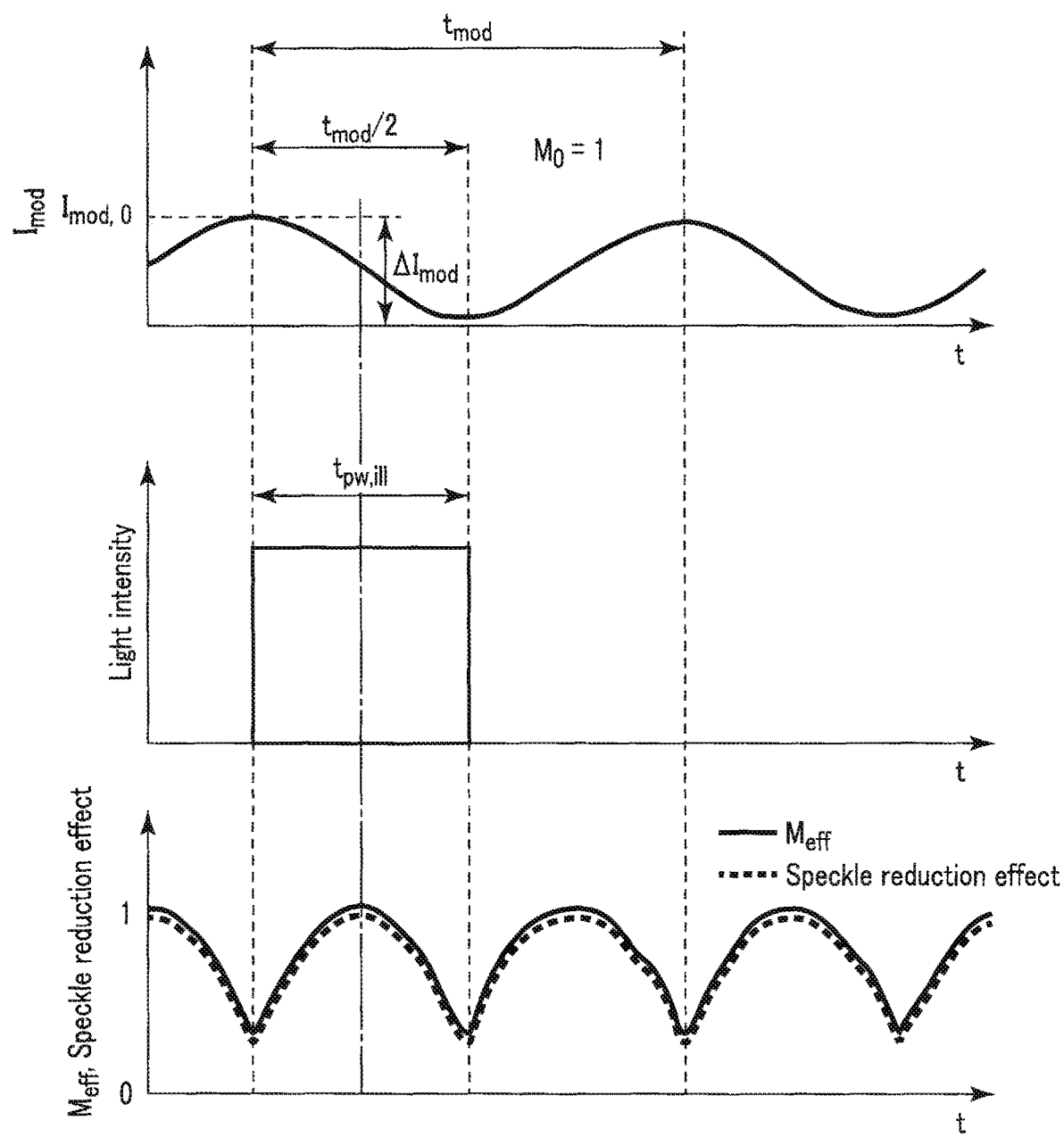
FIG. 3B2

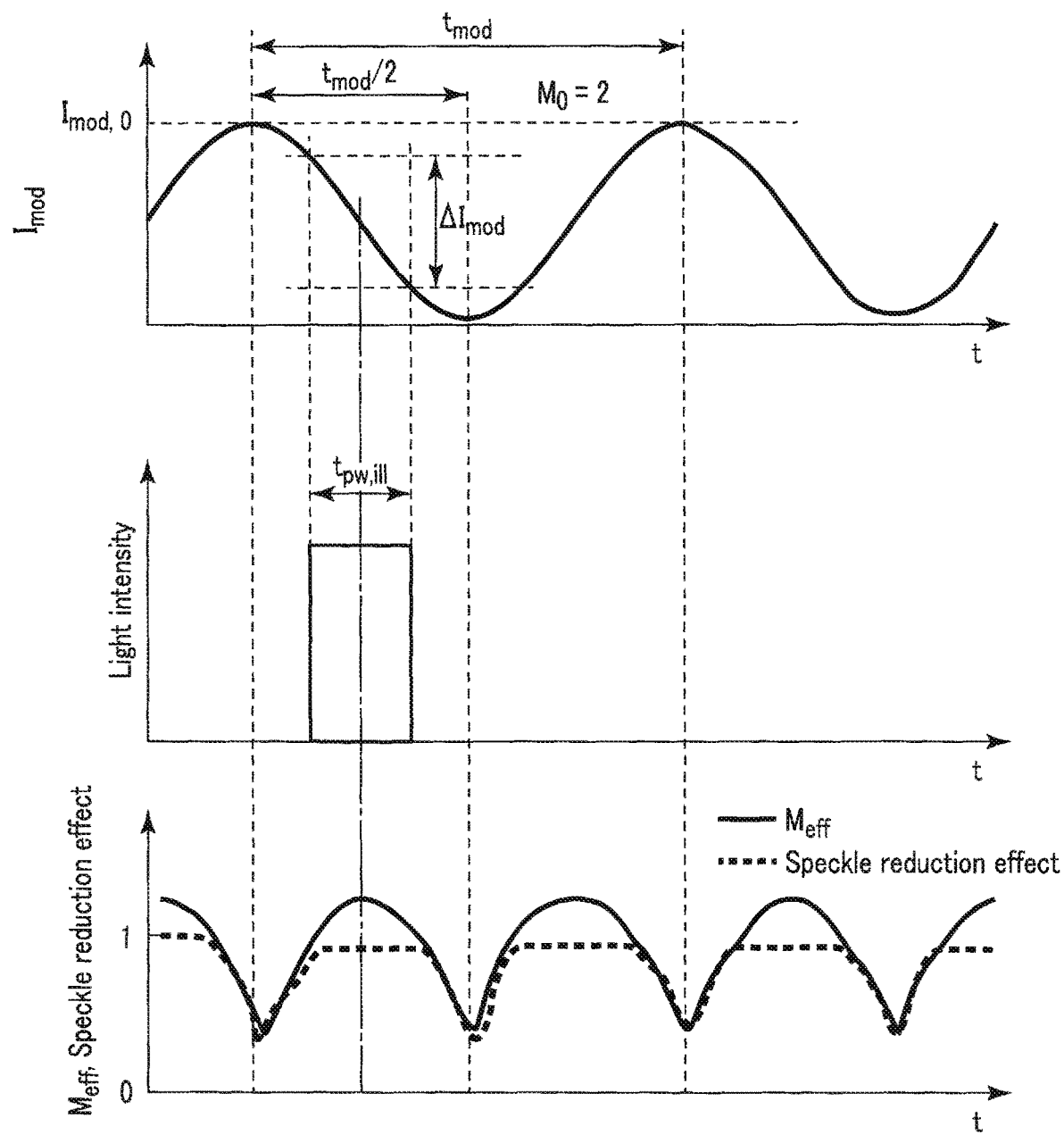
FIG. 3C1

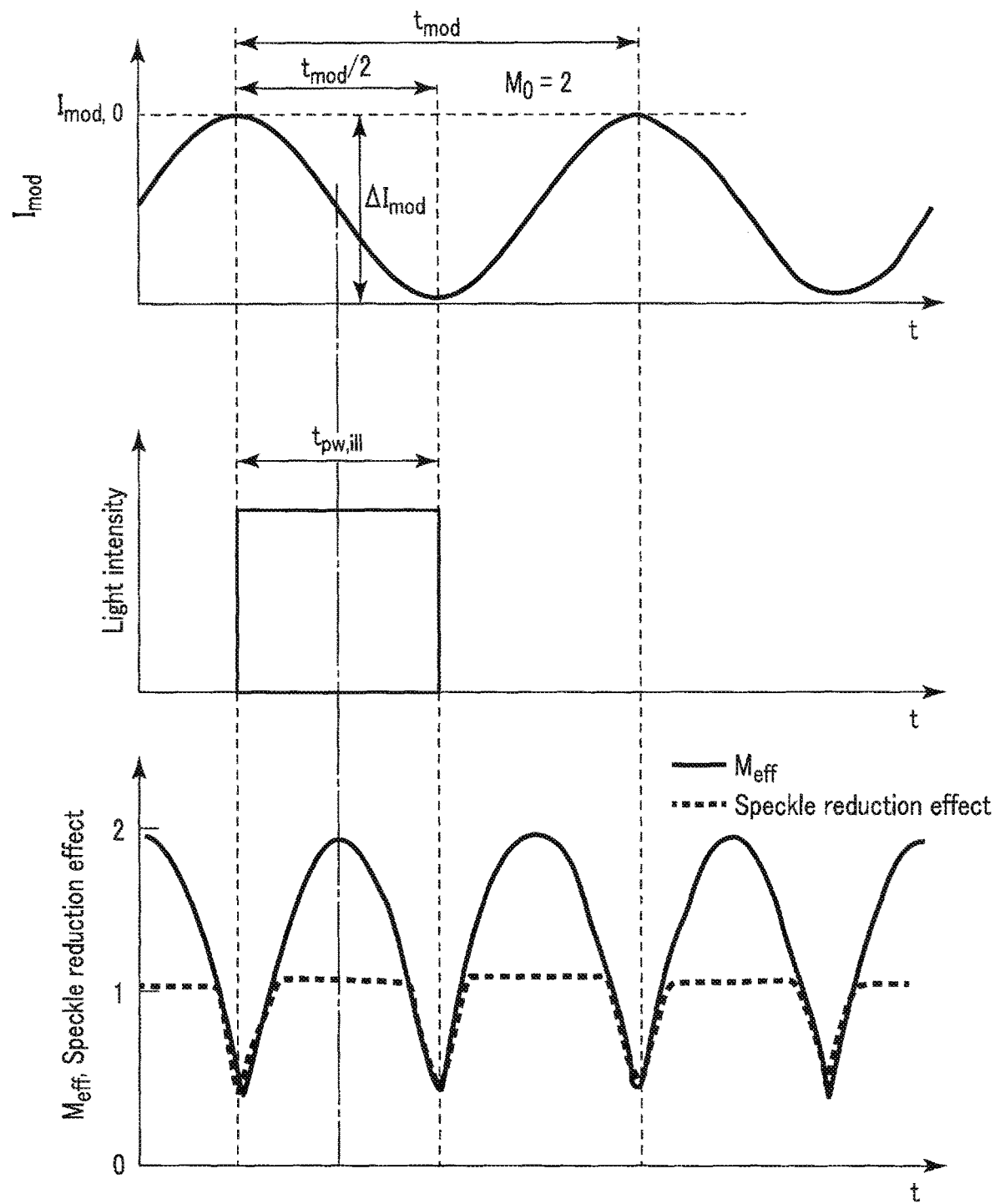
FIG. 3C2

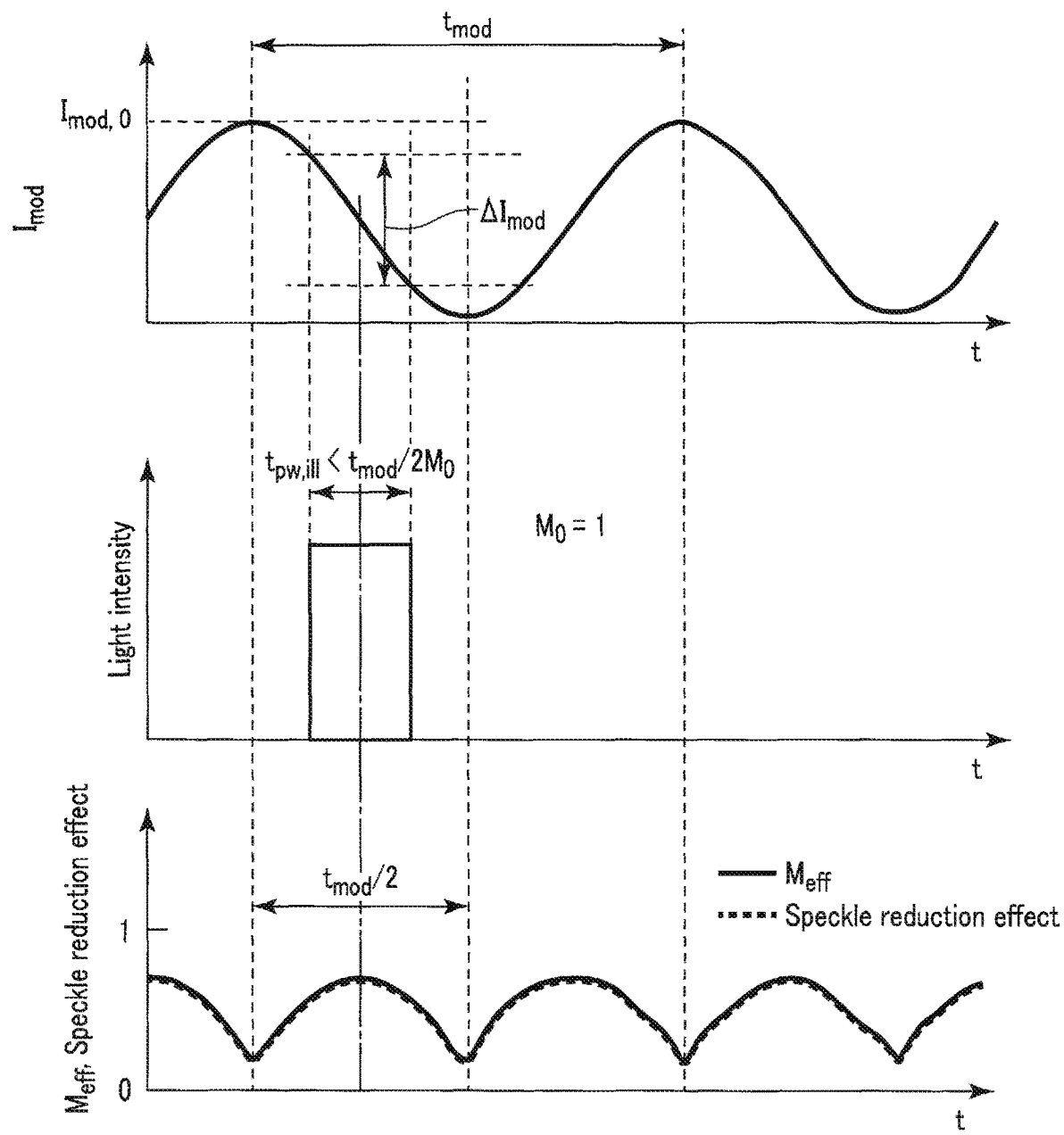
FIG. 4A1

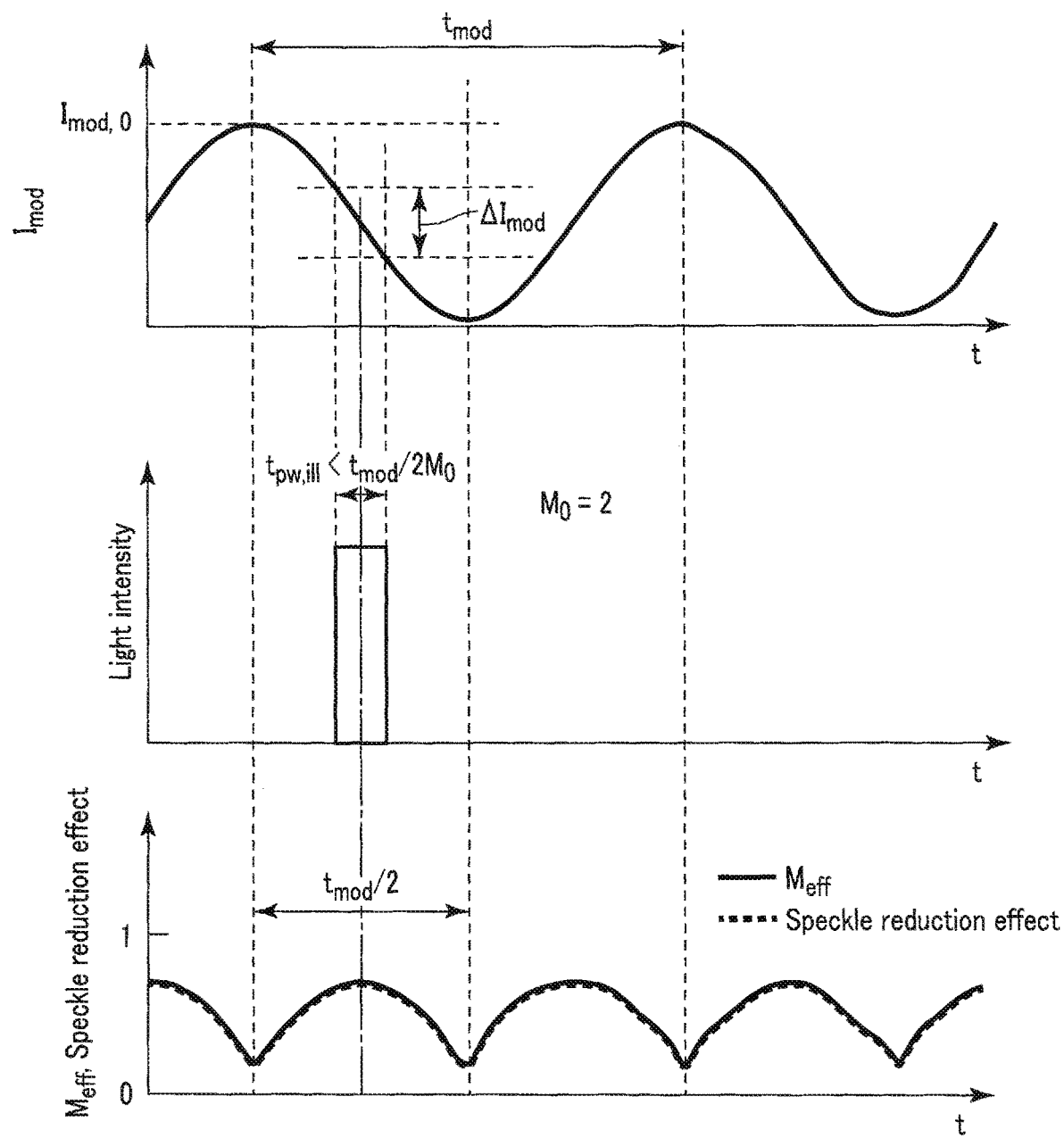
FIG. 4A2

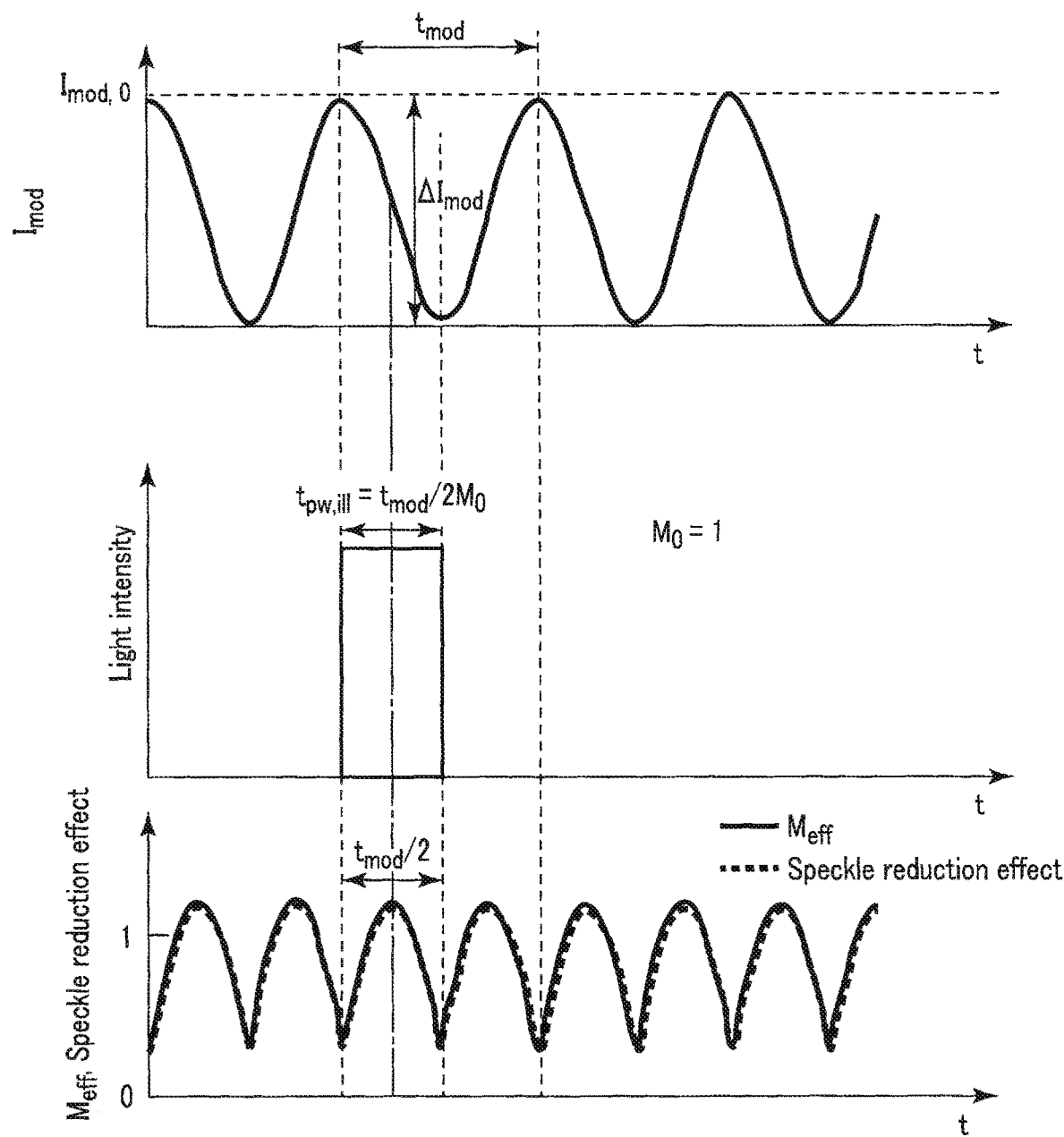
FIG. 4B1

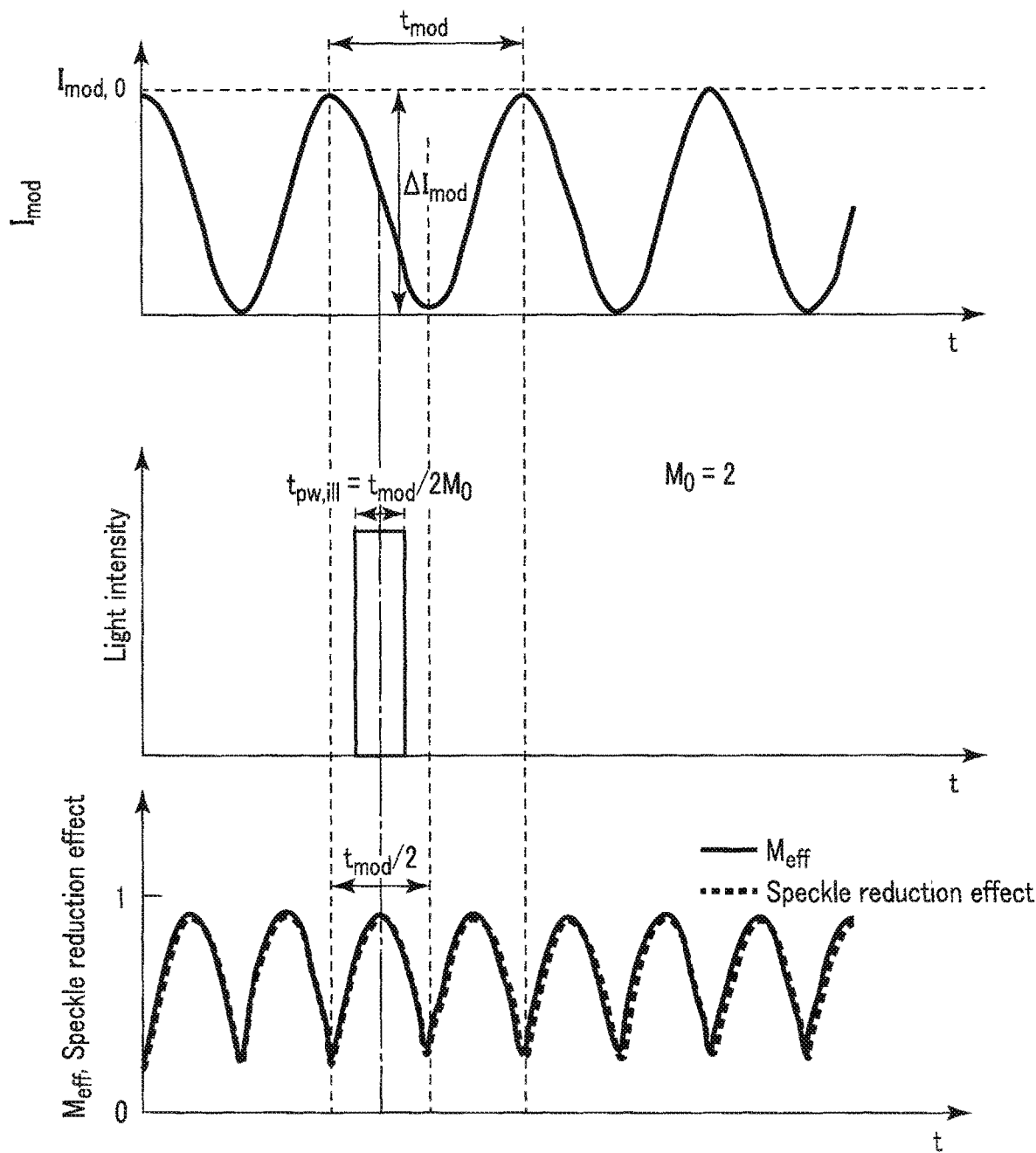
FIG. 4B2

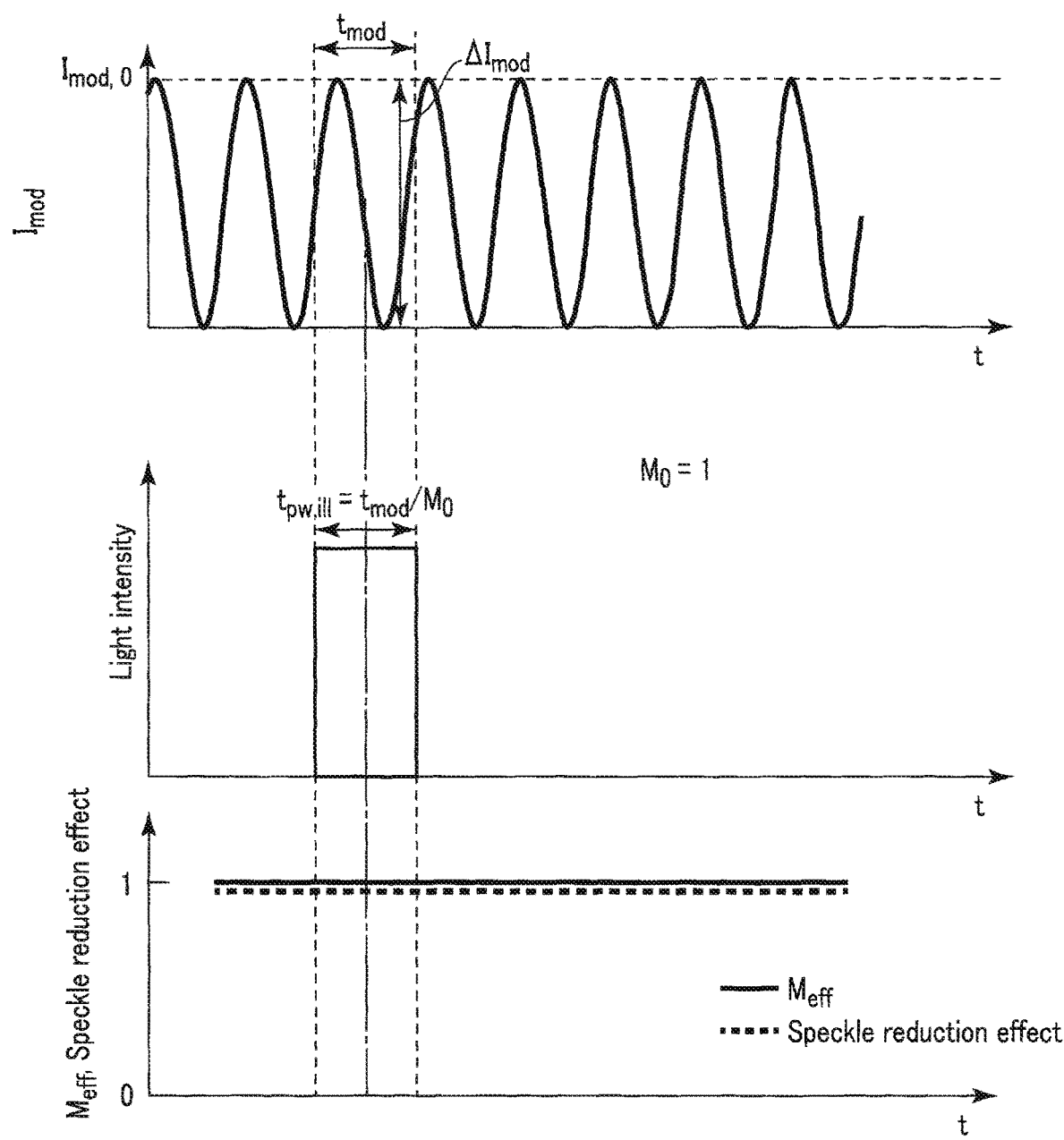
F I G. 4C1

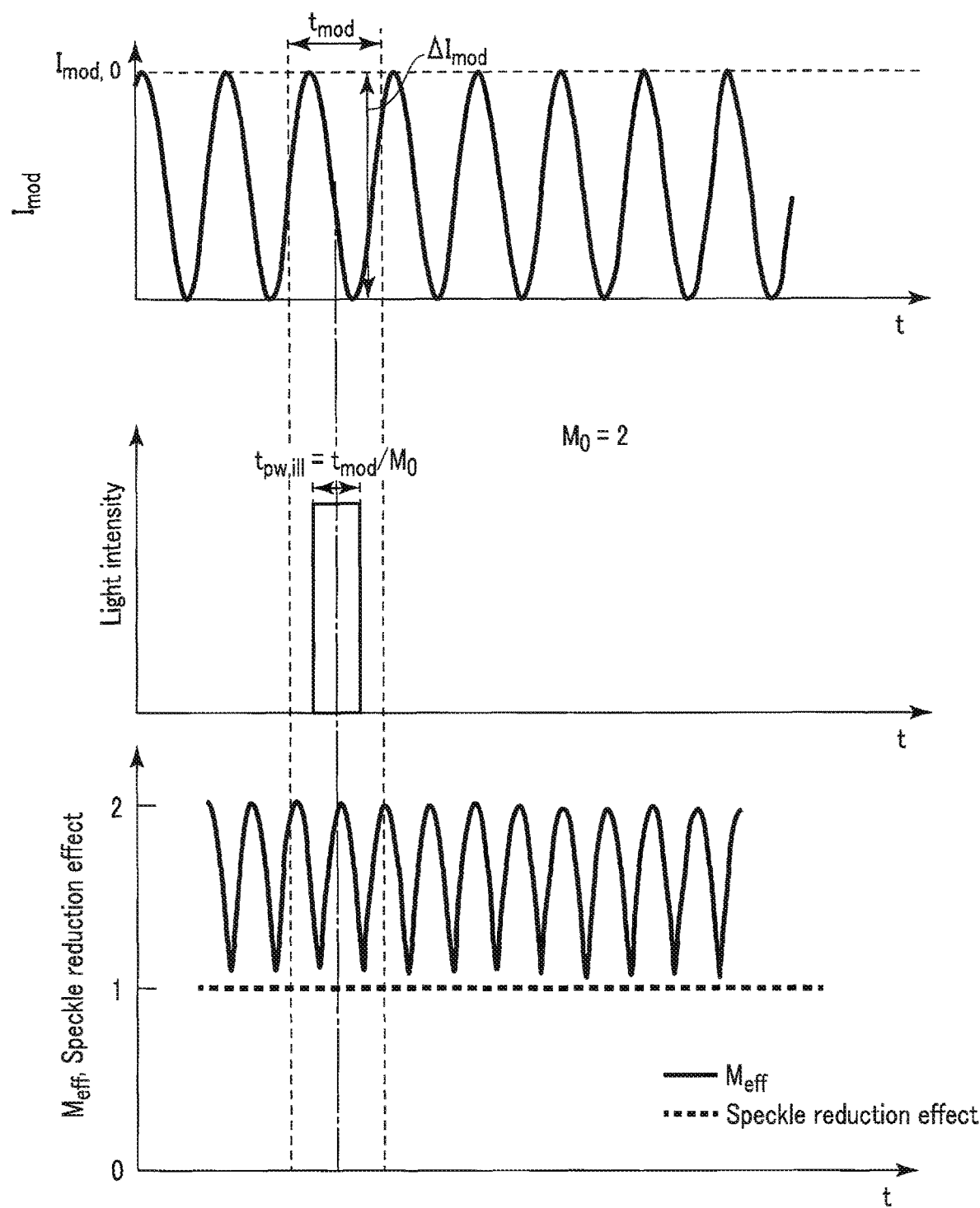
FIG. 4C2

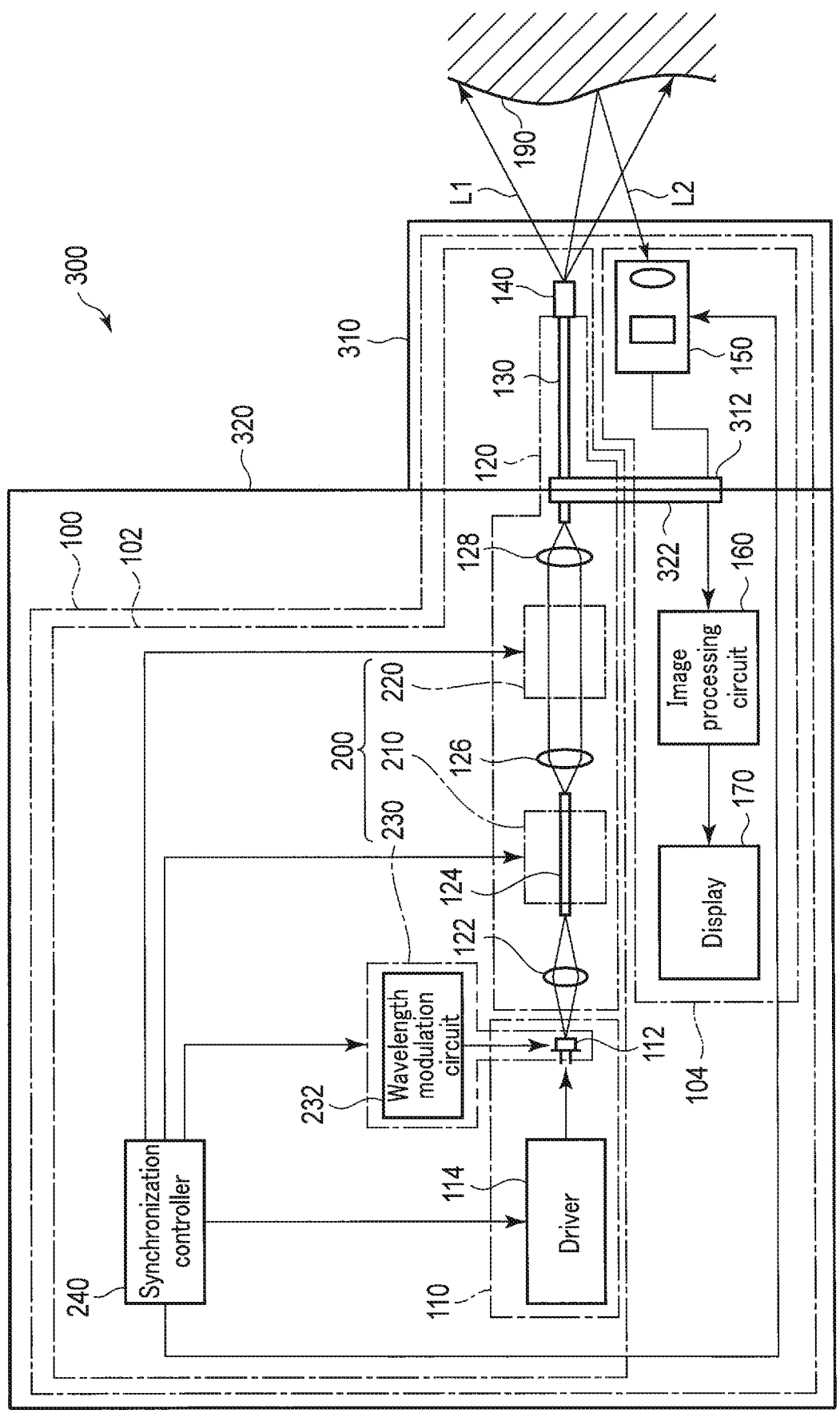
F I G. 5

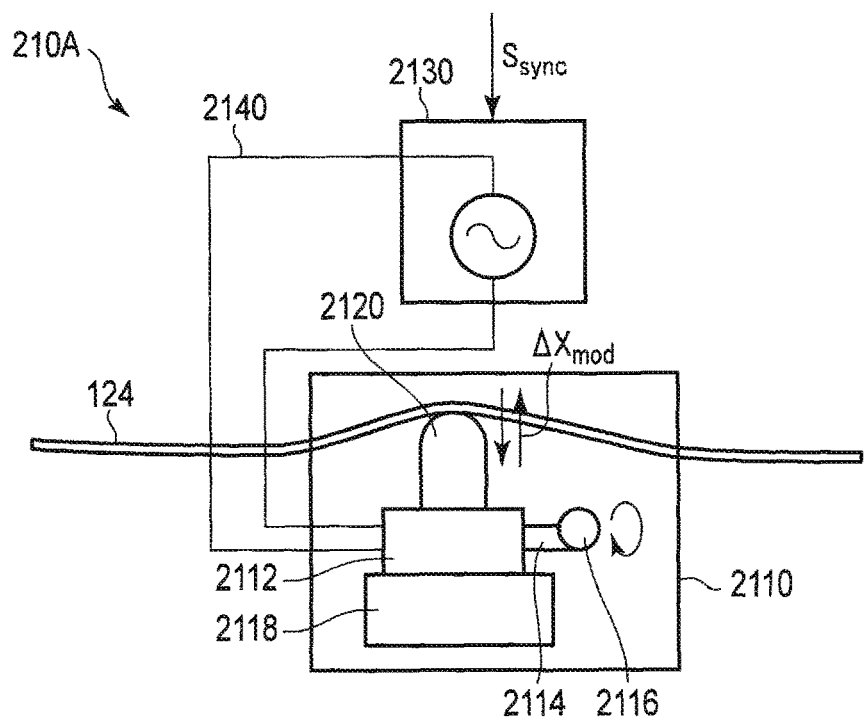
F I G. 6A
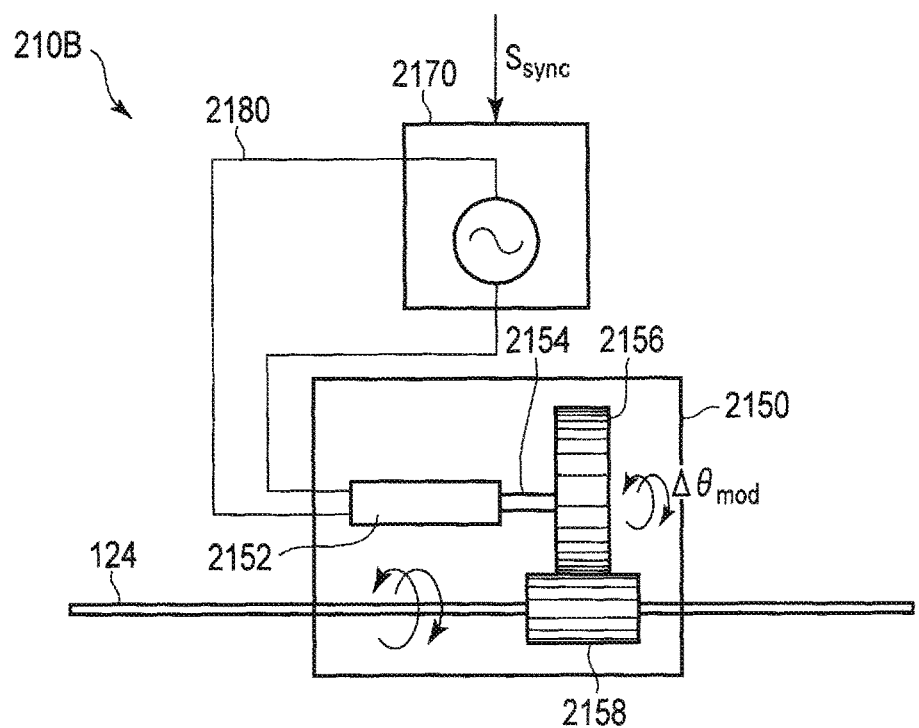
F I G. 6B

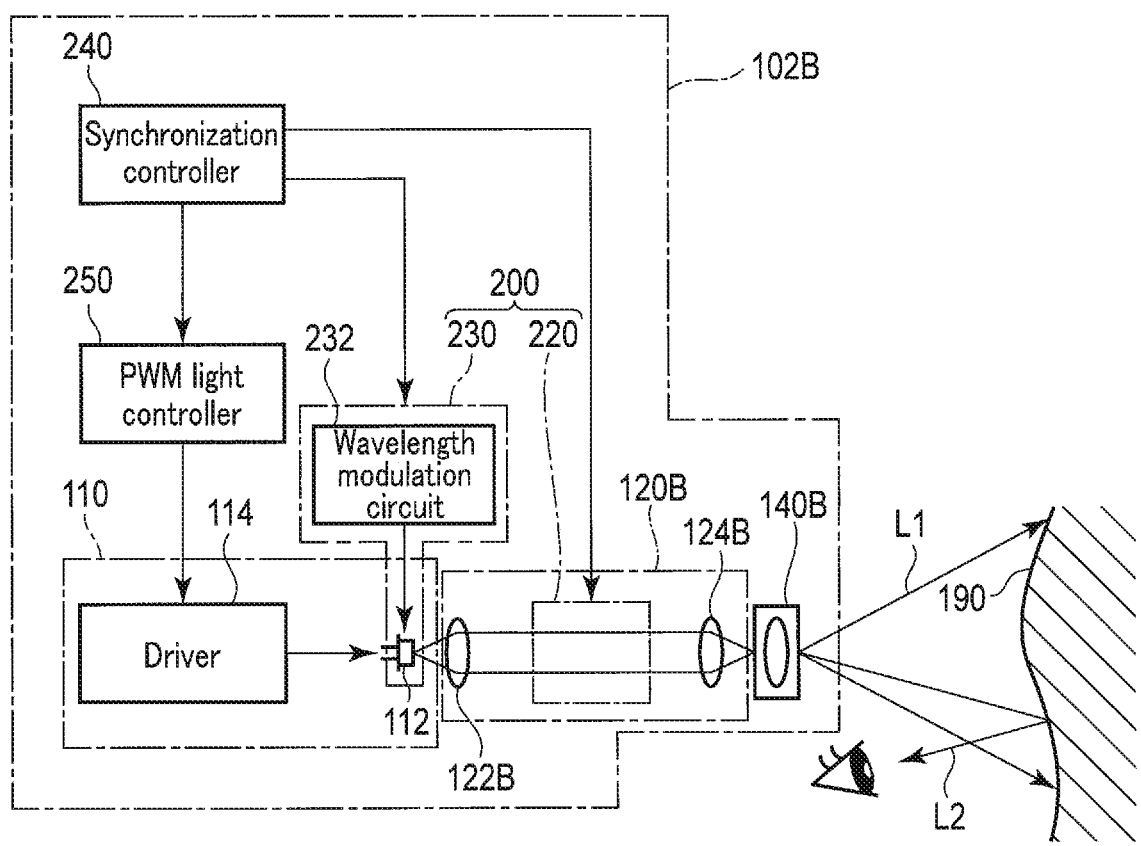
F I G. 10

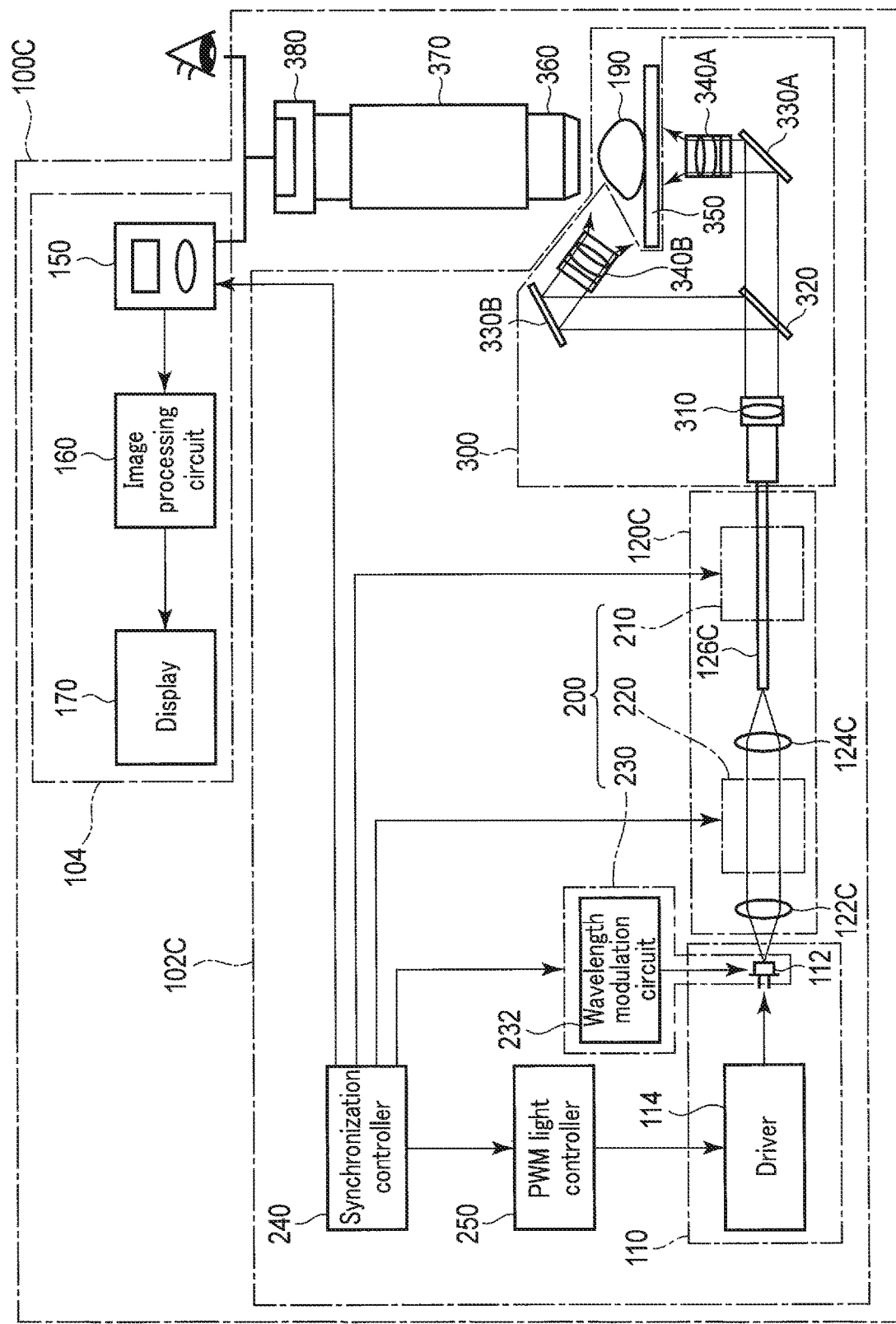
F I G. 11

ILLUMINATING DEVICE, IMAGING SYSTEM, ENDOSCOPE SYSTEM INCLUDING THE IMAGING SYSTEM, AND MICROSCOPE SYSTEM INCLUDING THE IMAGING SYSTEM

CROSS-REFERENCE TO RELATED APPLICATIONS

This application is a Continuation Application of PCT Application No. PCT/JP2017/018895, filed May 19, 2017, the entire contents of which are incorporated herein by reference.

BACKGROUND OF THE INVENTION

1. Field of the Invention

The present invention relates to an illuminating device using coherent light.

2. Description of the Related Art

In an imaging system that uses coherent light, typified by a laser light source, it is known that if an observation object has a scattering structure, such as subtle unevenness (concavo-convex), a fine speckle pattern (speckle) appears on the imaging surface of its imager, appears as noise (referred to as speckle noise) in an acquired image, hindering the visibility. This phenomenon is not limited to electronic imaging systems, but also occurs on the retina of a living body corresponding to an imaging surface, meaning that the same problem occurs in illuminating devices that use coherent light for illumination, e.g., a laser projector, etc. It is known that speckle is caused because light scattered from the unevenness (concavo-convex), etc. of an observation object interferes, and a fine light-dark pattern is formed on the imaging surface or the retina.

Various methods for reducing such speckle are known, and typical methods are listed below. In the following description, "coherent light" is often described as "laser light" as a representative example, but in this specification, this can also be referred to as general "coherent light". The general "coherent light" also includes "part of coherent light".

(1) [Method of reducing speckle noise by lowering the effective coherence of a light source itself]
(1-a) To promote a multimodal effect of a spectrum by performing high-frequency superposing for a driving waveform when the current of a laser diode (LD) is driven, thereby widening an effective spectral bandwidth.
(1-b) To mount a self-pulsation function on an LD, thereby disturbing a phase or a wavelength of light.
(1-c) To change the spectrum of wavelength-variable laser at high speed, thereby widening the effective spectrum bandwidth.
(1-d) To mutually combine a large number of independent lasers, thereby lowering the effective coherence.
(2) [Method of reducing effective coherence noise by temporally changing a light-dark pattern due to speckle and utilizing a temporal superposition effect of the contrast pattern]
(2-a) To vibrate an observation object, thereby changing its speckle pattern.
(2-b) To cause a change in an optical phase on an optical path from a light source to an observation object, thereby changing its speckle pattern.

As an example of the item (2-b), in a configuration where laser light is applied by guiding laser light through an optical fiber, a method is proposed in which a phase change of the laser light applied is caused by changing the shape or stress of the optical fiber to change a temporal light guide mode, thereby also changing a speckle pattern.

For example, Jpn. Pat. Appln. KOKAI Publication No. 2003-156698 discloses a laser light source device having such a configuration. In this laser light source device, laser light emitted from a laser light source enters an entrance end of an optical fiber and is then emitted as illumination light from an exit end of the optical fiber. At a middle part of the optical fiber, a vibration device configured to vibrate an optical fiber is provided. When the optical fiber is vibrated by the vibration device, a phase change of light due to a mode conversion of laser light occurs inside the optical fiber. Due to the change in characteristics of laser light (here, an optical phase change), a stripe pattern caused by speckle appearing when laser light is applied to an observation object from an optical fiber shifts or changes. This stripe pattern caused by speckle shifts or changes at a speed that cannot be detected by human eyes. Therefore, humans feel that stripe patterns caused by speckle are overlaid, and a resulting overlaid pattern is an averaged pattern, so that the speckle noise is reduced.

BRIEF SUMMARY OF THE INVENTION

An illuminating device according to the present invention includes an illumination light generator configured to generate illumination pulses of coherent light, and a speckle modulator configured to modulate speckle caused by the coherent light. The illumination pulse generator repeatedly generates a single illumination pulse group including a plurality of illumination pulses as a repetitive illumination pulse group.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A1 shows a driving waveform of a speckle modulator, an irradiation waveform of an illumination pulse generator optimally synchronized with the driving waveform, an effective amplitude modulation factor $M_{eff}$ serving as an indicator of speckle reduction effect, and the speckle reduction effect, and particularly shows a case where the pulse width of the irradiation waveform is shorter than a half period of the modulation period of the speckle modulator, and $M_0<1$.

FIG. 3A2 shows a driving waveform of the speckle modulator, an irradiation waveform of the illumination pulse generator optimally synchronized with the driving waveform, an effective amplitude modulation factor $M_{eff}$ serving as an indicator of speckle reduction effect, and the speckle reduction effect, and particularly shows a case where the pulse width of the irradiation waveform is equal to a half period of the modulation period of the speckle modulator, and $M_0<1$.

FIG. 3B1 shows a driving waveform of the speckle modulator, an irradiation waveform of the illumination pulse generator optimally synchronized with the driving waveform, an effective amplitude modulation factor $M_{eff}$ serving as an indicator of speckle reduction effect, and the speckle reduction effect, and particularly shows a case where the pulse width of the irradiation waveform is shorter than a half period of the modulation period of the speckle modulator, and $M_0=1$.

FIG. 3B2 shows a driving waveform of the speckle modulator, an irradiation waveform of the illumination pulse generator optimally synchronized with the driving waveform, an effective amplitude modulation factor $M_{eff}$ serving as an indicator of speckle reduction effect, and the speckle reduction effect, and particularly shows a case where the pulse width of the irradiation waveform is equal to a half period of the modulation period of the speckle modulator, and $M_0=1$.

FIG. 3C1 shows a driving waveform of the speckle modulator, an irradiation waveform of the illumination pulse generator optimally synchronized with the driving waveform, an effective amplitude modulation factor $M_{eff}$ serving as an indicator of speckle reduction effect, and the speckle reduction effect, and particularly shows a case where the pulse width of the irradiation waveform is shorter than a half period of the modulation period of the speckle modulator, and $M_0=2>1$.

FIG. 3C2 shows a driving waveform of the speckle modulator, an irradiation waveform of the illumination pulse generator optimally synchronized with the driving waveform, an effective amplitude modulation factor $M_{eff}$ serving as an indicator of speckle reduction effect, and the speckle reduction effect, and particularly shows a case where the pulse width of the irradiation waveform is equal to a half period of the modulation period of the speckle modulator, and $M_0=2>1$.

FIG. 4A1 shows a driving waveform of the speckle modulator, an irradiation waveform of the illumination pulse generator, an effective amplitude modulation factor $M_{eff}$ serving as an indicator of speckle reduction effect, and the speckle reduction effect, with respect to elapsed time, and shows a case where the amplitude modulation factor $M_0$ of the speckle modulator=1, and $t_{mod}/2M_0>t_{pw, ill}$.

FIG. 4A2 shows a driving waveform of the speckle modulator, an irradiation waveform of the illumination pulse generator, an effective amplitude modulation factor $M_{eff}$ serving as an indicator of speckle reduction effect, and the speckle reduction effect, with respect to elapsed time, and shows a case where the amplitude modulation factor $M_0$ of the speckle modulator=2>1, and $t_{mod}/2M_0>t_{pw, ill}$.

FIG. 4B1 shows a driving waveform of the speckle modulator, an irradiation waveform of the illumination pulse generator, an effective amplitude modulation factor $M_{eff}$ serving as an indicator of speckle reduction effect, and the speckle reduction effect, with respect to elapsed time, and shows a case where the amplitude modulation factor $M_0$ of the speckle modulator=1, and $t_{mod}/2M_0=t_{pw, ill}$.

FIG. 4B2 shows a driving waveform of the speckle modulator, an irradiation waveform of the illumination pulse generator, an effective amplitude modulation factor $M_{eff}$ serving as an indicator of speckle reduction effect, and the speckle reduction effect, with respect to elapsed time, and shows a case where the amplitude modulation factor $M_0$ of the speckle modulator=2>1, and $t_{mod}/2M_0=t_{pw, ill}$.

FIG. 4C1 shows a driving waveform of the speckle modulator, an irradiation waveform of the illumination pulse generator, an effective amplitude modulation factor $M_{eff}$ serving as an indicator of speckle reduction effect, and the speckle reduction effect, with respect to elapsed time, and shows a case where the amplitude modulation factor $M_0$ of the speckle modulator=1, and $t_{mod}/M_0=t_{pw, ill}$.

FIG. 4C2 shows a driving waveform of the speckle modulator, an irradiation waveform of the illumination pulse generator, an effective amplitude modulation factor $M_{eff}$ serving as an indicator of speckle reduction effect, and the speckle reduction effect, with respect to elapsed time, and shows a case where the amplitude modulation factor $M_0$ of the speckle modulator=2>1, and $t_{mod}/M_0=t_{pw, ill}$.

FIG. 5 schematically shows the overall configuration of an endoscope system including an imaging system according to a first embodiment.

FIG. 6A schematically shows the configuration of a light guide characteristic modulator configured to change the optical characteristic of laser light guided by a first optical fiber by vibrating the first optical fiber.

FIG. 6B schematically shows the configuration of a light guide characteristic modulator configured to change the optical characteristic of laser light guided by the first optical fiber by rotating the first optical fiber.

FIG. 10 schematically shows the overall configuration of an illuminating device according to a fourth embodiment.

FIG. 11 schematically shows the overall configuration of a microscope system including an imaging system according to a fifth embodiment.

DETAILED DESCRIPTION OF THE INVENTION

[Preparations for Discussing Effects of Primary Embodiments]

First, before discussing in detail the configuration and requirements for reducing speckle noise, a general mechanism of the speckle reduction effect obtained by an illuminating device or an imaging system by using a modulator of various optical characteristics of laser light will be described with reference to FIGS. 1A, 1B, 1C, 2A, 2B, and 2C. In this specification, a modulator having various optical characteristics including optical characteristics of light emitted from a light source itself for the purpose of reducing speckle, and changing the optical characteristics on an optical path from the light source to an observation object to thereby change the intensity or an intensity distribution of an observed speckle pattern, or causing positional shift, etc. of the speckle pattern, is referred to as a "speckle modulator".

In addition, in order to obtain the above-mentioned speckle reduction, the magnitude of the driving of the speckle modulator for causing modulation of various optical characteristics is defined as "driving intensity of a speckle modulator" and described as $I_{mod}$. Here, the "driving intensity of a speckle modulator" means, as specific examples, driving intensity of a wavelength modulation circuit of laser light for causing expansion or reduction in the effective optical spectral bandwidth of laser or an optical wavelength shift of the laser; driving intensity of a phase modulator for causing a change in the phase of light placed in the middle of the optical path configured to guide laser light from a light source to an observation object; driving intensity of a vibration device configured to generate a change in mechanical bend of an optical fiber, in order to change a phase of light in the case of using an optical fiber as an optical path configured to guide the light from a light source to an observation object; driving intensity of a stress applying device configured to change an applied stress to an optical fiber; driving intensity of a rotating device that delivers the twisting of an optical fiber, etc.

Figure 1A:
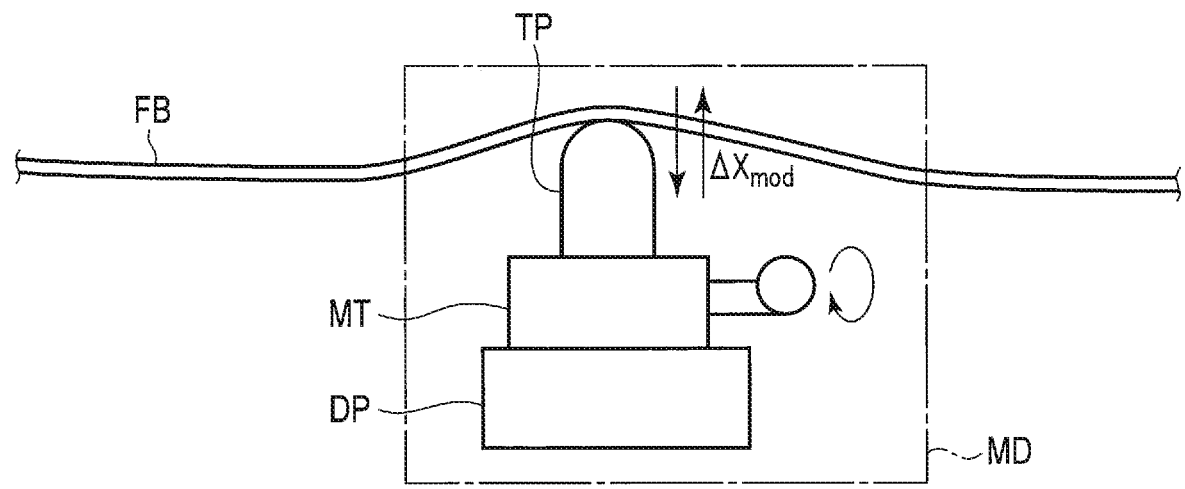
FIG. 1A shows a speckle modulator composed of a vibration device configured to vibrate an optical fiber.
Figure 1B:
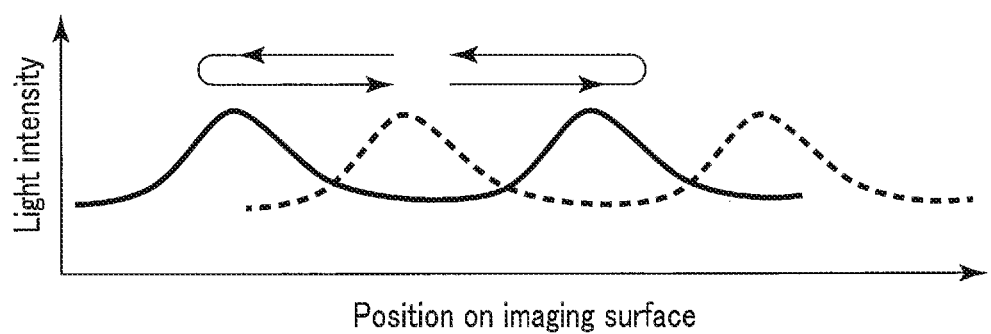
FIG. 1B shows a state that the vibration of the optical fiber temporally changes a phase or a mode of laser light in the optical fiber, so as to temporally change the speckle pattern.
Figure 1C:
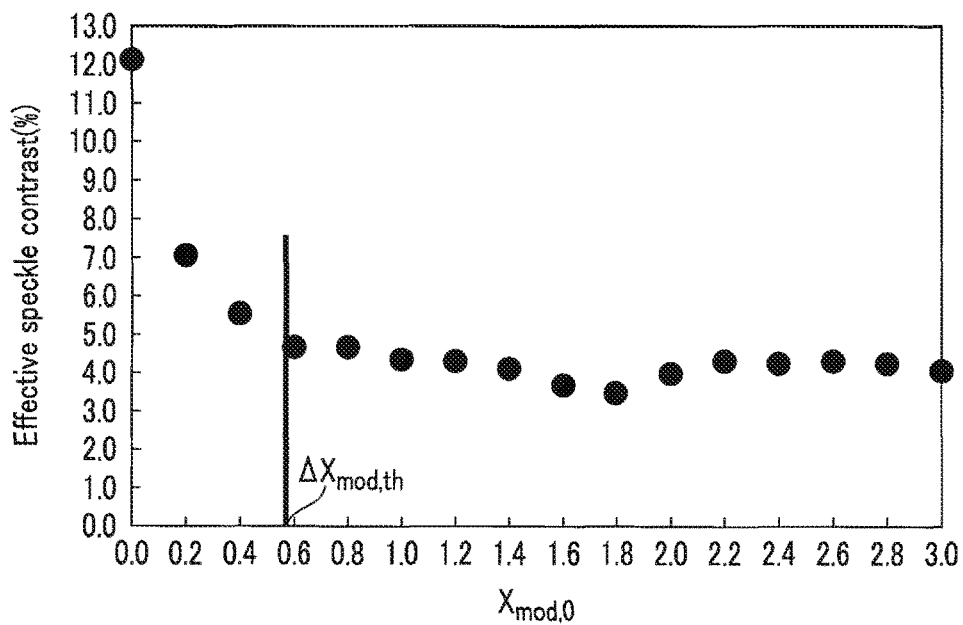
FIG. 1C is a result of an experiment actually conducted by the present inventors and shows a result of measuring a change in effective speckle contrast with respect to a vibration amplitude $X_{mod,\,0}$ of the optical fiber.

FIGS. 1A to 1C illustrate a speckle reduction mechanism by mechanically vibrating an optical fiber that is present in an optical path of laser light from a laser light source to an observation object.

FIG. 1A shows a speckle modulator composed of a vibration device configured to vibrate an optical fiber. A vibration motor MT is placed on a fixing member (not shown) through a damper DP configured to absorb vibration. A weight having a center of gravity that is asymmetric with respect to a rotation axis of the vibration motor MT is attached to the rotation axis. An abutting member TP is fixed to the vibration motor MT. The abutting member TP is in contact with an optical fiber FB. When the rotation axis of the vibration motor MT rotates, the vibration motor MT also vibrates. This vibration is transmitted to the optical fiber FB through the abutting member TP. As a result, the optical fiber FB is vibrated.

As described above, by vibrating the optical fiber FB, it is possible to temporally change the phase or the mode of laser light in the optical fiber FB and to temporally change a speckle pattern (FIG. 1B). Within one imaging frame time, since an image formed on the imaging surface is observed in a state where speckle patterns that temporally change are overlapping with one another, the speckle patterns are averaged, reducing effective speckle noise on the imaging surface. As shown in FIG. 1B, when it is considered that a change (or an amount of shift) of the speckle pattern within the imaging time is sufficiently large and the superposition of the speckle pattern within the imaging time is sufficiently averaged, the speckle reduction effect resulting from superposition of speckle patterns on a time average is saturated, even if the vibration amplitude is further increased.

FIG. 1C shows a result of an experiment actually conducted by the present inventors. Specifically, FIG. 1C shows a result of measuring an effective change in speckle contrast with respect to a vibration amplitude $X_{mod, 0}$ of the optical fiber. Consistent with the prediction in connection with FIG. 1B, a result has been obtained in which the vibration amplitude reached its maximum in the vicinity of a certain threshold $\Delta X_{mod, th}$, and even when the amplitude has been increased further, the speckle reduction effect has been saturated without significant change. This experiment saw the evaluation of a speckle contrast obtained when imaging has been performed for a lengthy period so that speckle patterns have been sufficiently overlapped within the imaging time.

Figure 2A:
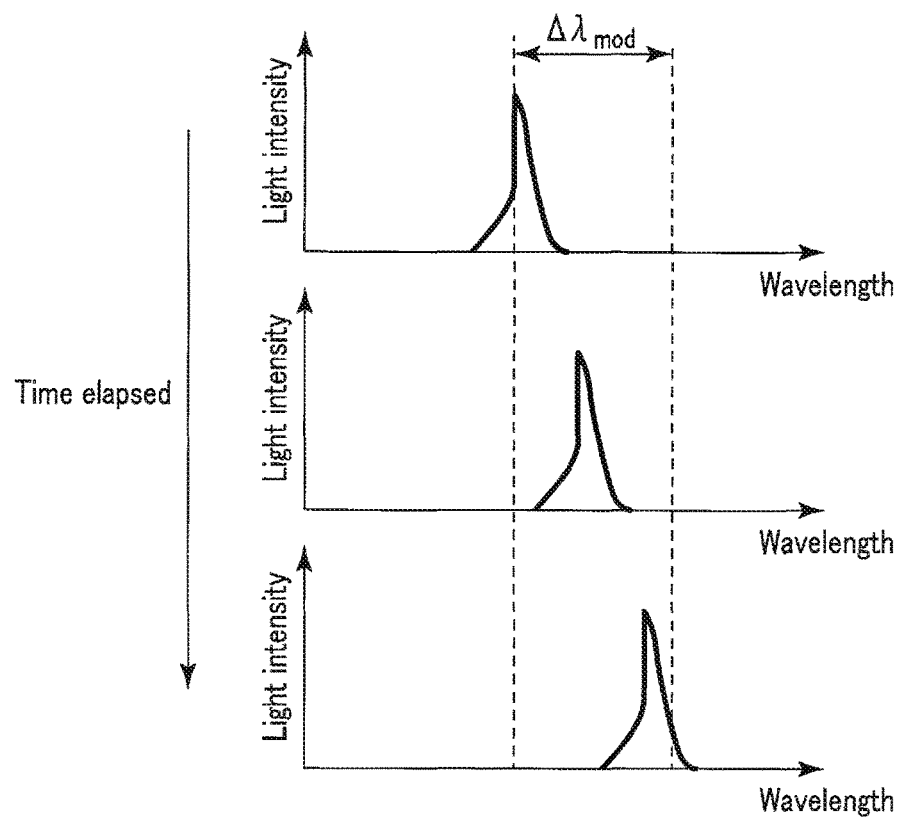
FIG. 2A shows spectra of laser light in which the wavelength is temporally changed with a change width $\lambda_{mod}$.
Figure 2B:
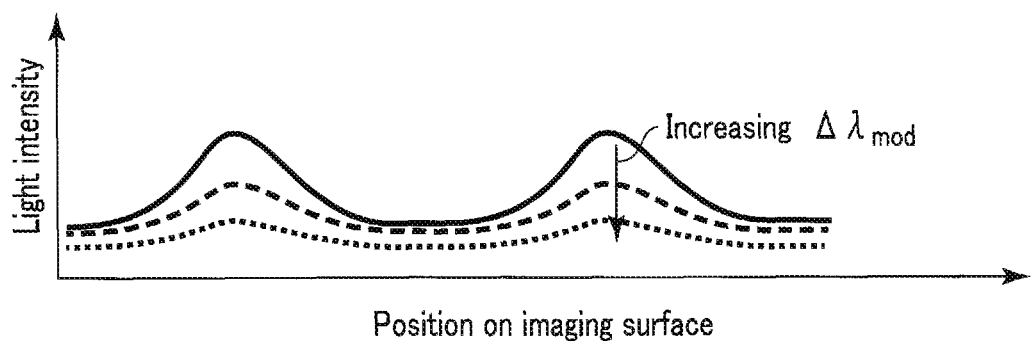
FIG. 2B shows one-dimensional light intensity distributions of a speckle pattern corresponding to the wavelength change width $\lambda_{mod}$ of the laser light shown in FIG. 2A.
Figure 2C:
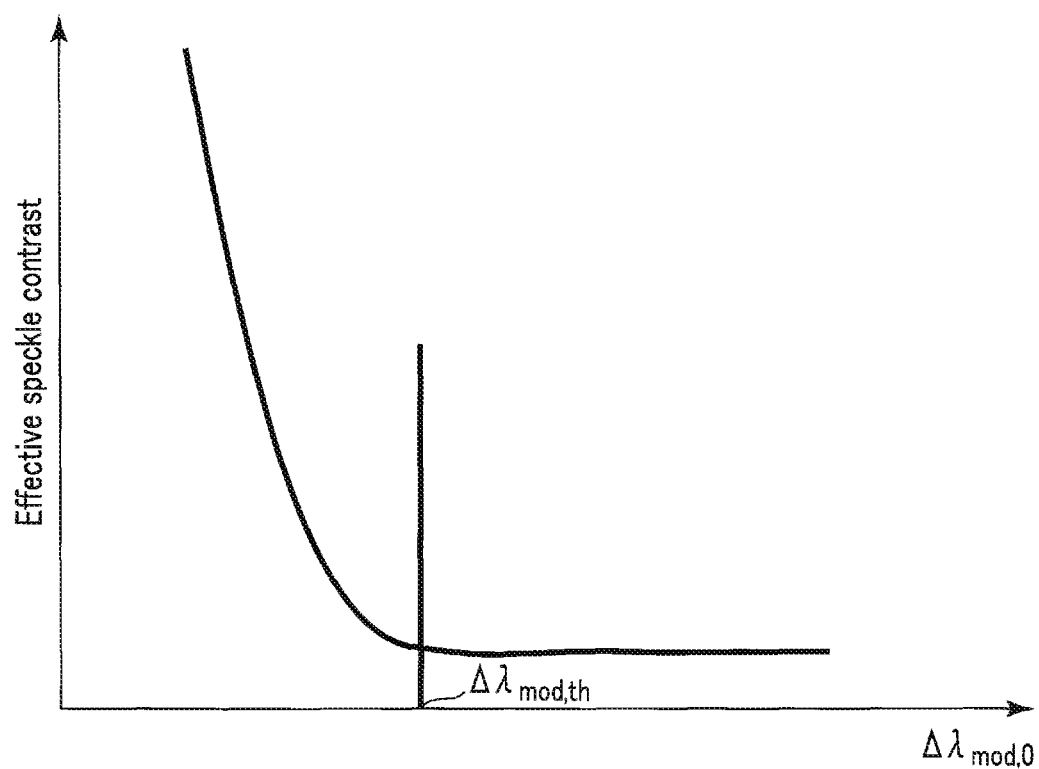
FIG. 2C shows a change in effective speckle contrast with respect to a change width $\Delta\lambda_{mod, 0}$ of the wavelength change width of the laser light.

FIG. 2A shows spectra of laser light whose wavelength has been temporally changed with a change width $\lambda_{mod}$. FIG. 2B shows one-dimensional light intensity distributions of a speckle pattern corresponding to a change width $\lambda_{mod}$ of the wavelength of the laser light shown in FIG. 2A. FIG. 2C shows a change in effective speckle contrast with respect to a change width $\Delta\lambda_{mod, 0}$ of the wavelength change width of the laser light. As shown in FIGS. 2B and 2C, when the wavelength change width $\lambda_{mod}$ of the laser light is increased, the light intensity distribution resulting from a speckle phenomenon is reduced (that is, the speckle contrast is reduced). This is because the speckle modulator modulates the wavelength of laser light, and the bandwidth of the wavelength of the laser light appears to expand, which corresponds to effectively reducing the coherence of the laser light. A threshold $\Delta\lambda_{mod, th}$ corresponding to the wavelength change width for saturating the speckle reduction effect is determined by the resolution of an imaging optical system or an imager, but similarly to the case of FIGS. 1A to 1C, the speckle reduction effect exhibits minimal change even when the wavelength is further changed within the imaging time.

In this specification, in order to discuss various effects of a speckle modulator for reducing speckle in a summarized and more generalized manner, a driving intensity of a speckle modulator is denoted by $I_{mod}$, a driving intensity amplitude is denoted by $I_{mod, 0}$, and a time period when the speckle modulator is periodically driven is denoted by a speckle modulation period $t_{mod}$, regardless of the speckle modulator for reducing speckle noise. In addition, a width of the driving intensity corresponding to the condition under which the reduction in speckle contrast is substantially maximum, and the speckle reduction effect is saturated even if a further driving intensity is applied is denoted by a driving intensity threshold width $\Delta I_{mod,\ th}$ of the speckle modulator, and a change width of the driving intensity of the speckle modulator corresponding to an exposure period of the imager within one imaging frame time is denoted by $\Delta I_{mod}$. (It is also possible to control the light quantity by pulse width modulation (PWM) by limiting the exposure period (or light accumulation period) $t_{pw,\ exp}$ of the imager, instead of limiting the pulse emission period $t_{pw,\ ill}$ of the light source within the imaging frame time; in this case, the change width of the driving intensity within the exposure period $t_{pw,\ exp}$ is $\Delta I_{mod}$). Furthermore, a value obtained by standardizing the driving intensity amplitude $I_{mod,\ 0}$ of the speckle modulator with the driving intensity threshold width $\Delta I_{mod,\ th}$ of the speckle modulator is denoted by a amplitude modulation factor $M_0$, and a value obtained by standardizing the change width $\Delta I_{mod}$ of the driving intensity of the speckle modulator with $\Delta I_{mod,\ th}$ is denoted by an effective amplitude modulation factor $M_{eff}$.

According to the above discussion, in general, if the speckle modulator is driven at a sufficiently fast period with respect to an exposure available period $t_{ON}$ of the imager within one imaging frame or a pulse emission period $t_{pw,\ ill}$ of the light source, or if the imaging timing of the imager, the drive timing of the speckle modulator, and the irradiation timing of the laser light are optimally synchronized, as the change width $\Delta I_{mod}$ of the speckle modulator driving intensity is increased, the speckle reduction effect increases monotonically until $\Delta I_{mod}$ reaches $\Delta I_{mod,\ th}$, and the speckle reduction effect is saturated in the vicinity in which $\Delta I_{mod}$ becomes $\Delta I_{mod,\ th}$. In addition, if the effective amplitude modulation factor $M_{eff}$ is increased by increasing the change width $\Delta I_{mod}$ of the driving intensity of the speckle modulator, the speckle reduction effect also increases monotonically with $M_{eff}$, and it is considered that in the case of operating a single speckle reduction mechanism, the speckle reduction effect is almost saturated when $M_{eff} \geq 1$.

Since the driving intensity threshold width $\Delta I_{mod,\ th}$ is 0.1 mm in terms of the displacement in vibration of a light guide variation device (to be described later) configured to apply a mechanical change to the optical fiber as a light guide, the driving intensity amplitude $I_{mod,\ 0}$ of the speckle modulator is preferably 0.1 mm or more in terms of the displacement of vibration of the optical fiber caused by the light guide variation device. Since the driving intensity amplitude $I_{mod,\ 0}$ of the speckle modulator has been about 5 times the core diameter $\Phi c=0.02$ mm of the optical fiber at the time of the experiment, it is considered that the driving intensity amplitude $I_{mod,\ 0}$ of the speckle modulator is desirably $5\Phi c$ or more in terms of the displacement of the optical fiber due to the vibration of the light guide variation device.

Furthermore, since the driving intensity threshold width $\Delta I_{mod,\ th}$ is 10° in terms of an angle at which the optical fiber (to be described later) is twisted, the driving intensity amplitude $I_{mod,\ 0}$ of the speckle modulator is preferably 10° or more in terms of an angle at which the optical fiber is twisted.

In addition, when a change in refractive index of a refractive index modulator (electro-optic element, acousto-optic element), which will be described later, is used as a speckle modulator, when light is passing through the refractive index modulator, a change corresponding to one wavelength ($2\pi$ in phase) is considered to correspond to the driving intensity threshold width $\Delta I_{mod,\ th}$. That is, it is preferable to modulate the refractive index with $Lm \cdot \Delta n/n/\lambda c \geq 1$, where $\lambda$ is an optical wavelength, Lm is a length of the refractive index modulator on the optical axis, n is a refractive index, and $\Delta n$ is the amount of change in the refractive index. Therefore, the driving intensity amplitude $I_{mod,\ 0}$ of the speckle modulator is preferably $\Delta n/n \geq \lambda c/Lm$ in terms of a change in refractive index of the refractive index modulator, where Lm is a length of the refractive index modulator in the light guide direction, $\Delta n/n$ is a change in refractive index, and $\lambda c$ is a center wavelength of a spectrum of an illumination pulse. As a typical example, when Lm=5 mm and $\lambda c=0.5$ μm, the amount of change in refractive index corresponds to approximately 0.01%.

[Definitions of Terms Used to Discuss Effects of Speckle Modulators in Summarized Manner]

<$I_{mod}$: Driving Intensity of Speckle Modulator>

Specifically, the driving intensity of a speckle modulator means driving intensity of a laser wavelength modulation circuit to expand the effective optical spectrum bandwidth of the laser or to shift the optical wavelength; driving intensity of an optical phase modulator disposed in the middle of the optical path guiding laser light from a light source to an observation object; a mechanical bending strength, an applied stress strength, a bending strength, etc. for changing an optical phase on the optical path when using an optical fiber as the optical path configured to guide laser light from a light source to an observation object.

<$I_{mod,\ 0}$: Driving Intensity Amplitude of Speckle Modulator>

When the speckle modulator is driven periodically, the driving intensity amplitude results in $I_{mod,\ 0} = I_{mod,\ max} - I_{mod,\ min}$, where $I_{mod,\ max}$ is a maximum value of the driving intensity of the speckle modulator, and $I_{mod,\ min}$ is a minimum value.

<$T_{mod}$: Speckle Modulation Period>

The speckle modulation period is a time period when the speckle modulator is driven periodically.

<$\Delta I_{mod}$: Change Width of Driving Intensity of Speckle Modulator>

In the imaging system, the change width $\Delta I_{mod}$ of driving intensity of the speckle modulator is a change width of driving intensity of the speckle modulator within an exposure period of the imager (or within a light accumulation period of the imager) in one imaging frame. In an illuminating device without an imager, the change width $\Delta I_{mod}$ of driving intensity of the speckle modulator is a change width of the driving intensity of the speckle modulator within a time period considered to be a response time to an image change of a living body (33 msec when the living body is a human being).

<$\Delta I_{mod,\ th}$: Driving Intensity Threshold Width of Speckle Modulator>

The driving intensity threshold width $\Delta I_{mod,\ th}$ of speckle modulator is a change width of the driving intensity for saturating the speckle reduction effect when increasing the driving intensity of the speckle modulator.

<$M_0$: Modulation Vibration Factor>

$M_0 = I_{mod,\ 0}/\Delta I_{mod,\ th}$

<$M_{eff}$: Effective Amplitude Modulation Factor>

$M_{eff} = \Delta I_{mod}/\Delta I_{mod,\ th}$

Since $M_{eff}$ has a positive correlation with the speckle reduction effect, this can be used as an indicator of the speckle reduction effect. In the case of operating a single speckle reduction mechanism, the speckle reduction effect is almost saturated when $M_{eff} \geq 1$.

FIGS. 3A1 and 3A2, FIGS. 3B1 and 3B2, and FIGS. 3C1 and 3C2 each illustrate a relationship between "a driving vibration of the speckle modulator" and "$M_{eff}$ and the speckle reduction effect" with respect to the above-described imaging timing, the illumination timing, and the modulation timing. FIGS. 3A1 and 3A2 each show a case where $M_0<1$, FIGS. 3B1 and 3B2 each show a case where $M_0=1$, and FIGS. 3C1 and 3C2 each show a case where $M_0=2>1$. In FIGS. 3A1 and 3A2, FIGS. 3B1 and 3B2, and FIGS. 3C1 and 3C2, the upper part shows a driving waveform of the speckle modulator with respect to elapsed time; the middle part shows, on a time axis, an irradiation waveform of the illumination pulse generator optimally synchronized with the driving waveform; and the lower part shows $M_{eff}$ serving as an indicator of speckle reduction effect and the speckle reduction effect, with respect to the center time of the irradiation timing of the illumination pulse generator. Here, $M_{eff}$ corresponds to an integrated value of the irradiation waveform at the center time of the irradiation timing. Furthermore, FIGS. 3A1, 3B1, and 3C1 each show a case where the pulse width (i.e., a pulse emission period) $t_{pw, ill}$ of the irradiation waveform is shorter than a half period of the modulation period of the speckle modulator ($t_{mod}/2 > t_{pw, ill}$). FIGS. 3A2, 3B2, and 3C2 show a case where the pulse width (i.e., a pulse emission period) $t_{pw, ill}$ of the irradiation waveform is equal to a half period of the modulation period of the speckle modulator ($t_{mod}/2 = t_{pw, ill}$). In FIGS. 3A1 and 3A2, FIGS. 3B1 and 3B2, and FIGS. 3C1 and 3C2, a numerical value of the speckle reduction effect is indicated after being standardized in a speckle contrast in which the numerical value is proportional to an inverse number of the speckle contrast, and the speckle reduction effect brought about by the speckle modulator is at its greatest. For this reason, the numerical value of the speckle reduction effect is plotted so as to be 1 under the condition that the reduction effect brought about by the speckle modulator is saturated and reaches a maximum.

Through the above description, it is preferable that the exposure timing of the imager be synchronized with the irradiation timing. The exposure period needs to include at least a part of the irradiation period; preferably all of the irradiation periods. (Not necessarily synchronized. For example, should a relationship in which an irradiation pulse is present one or more times during the $t_{pw, exp}$ be established, the speckle reduction effect can be obtained even if the exposure timing and the irradiation timing are not synchronized.)

Conversely, when PWM is used during an exposure period of the imager, the same speckle reduction effect can be obtained by replacing the emission period $t_{pw, ill}$ of the light source with an emission period $t_{pw, ill}$ of the imager throughout FIGS. 3A1 and 3A2, 3B1 and 3B2, and 3C1 and 3C2. In this case, needless to say, the emission period $t_{pw, ill}$, conversely, must include a part or all of $t_{pw, exp}$.

The same applies to FIGS. 4A1 and 4A2, FIGS. 4B1 and 4B2, and FIGS. 4C1 and 4C2 to be described later.

The summary of what can be seen from FIGS. 3A1 and 3A2, FIGS. 3B1 and 3B2, and FIGS. 3C1 and 3C2 is as follows.

When the driving amplitude or driving width of the speckle modulator is increased so as to increase $M_0$ or $M_{eff}$, the speckle reduction effect is increased monotonically.

Speaking on a time axis, when the speckle modulator and the illumination pulse generator are synchronized so as to increase the change width $\Delta I_{mod}$ of the driving intensity of the speckle modulator, the speckle reduction effect reaches a maximum.

When the imaging timing, the illumination timing, and the modulation timing are optimized by setting $M_{eff} \geq 1$, the speckle reduction effect can be increased to a maximum. Furthermore, under the condition of $M_{eff} \geq 1$, a stable speckle reduction effect is obtained in which the speckle reduction effect is saturated with small timing dependency of imaging, illumination, and modulation.

For this reason, a synchronization controller is provided in order to optimize the drive timing of the speckle modulator, the illumination timing, and the imaging timing to thereby increase $M_{eff}$ and sufficiently extract the speckle reduction effect. Here, the illumination timing means temporal timing of a pulse emission period generated by the illumination pulse generator, and the imaging timing means light-receiving timing of the imager within one imaging frame.

As a method of performing the synchronization control for optimizing the imaging timing, the illumination timing, and the drive timing of the speckle modulator described above, the following synchronization methods can be used: 1) a method in which the imaging timing is used as the master time, and the illumination timing and the drive timing of the speckle modulator are synchronized with the master time at predetermined timing; 2) a method in which the illumination timing is used as the master time, and the imaging timing and the drive timing of the speckle modulator are synchronized with the master time at predetermined timing; 3) a method in which the drive timing of the speckle modulator is used as the master time, and the imaging timing and the illumination timing are synchronized with the master time at predetermined timing; 4) a method in which a system clock of an illuminating device or an imaging system is used as the master time, and the imaging timing, the illumination timing, and the drive timing of the speckle modulator are synchronized with the master time, etc.

Furthermore, on the condition that these periods can all be synchronized, an imaging period (frame rate) $1/f_r$, an illumination pulse generation period $t_p$, and a driving period $t_{mod}$ of the speckle modulator are not necessarily the same.

FIGS. 4A1 and 4A2, FIGS. 4B1 and 4B2, and FIGS. 4C1 and 4C2 each illustrate a relationship between "a modulation rate of the speckle modulator" and "$M_{eff}$, and the speckle reduction effect", using the above-described imaging timing, illumination timing, modulation timing, and amplitude modulation factor $M_0$ of the speckle modulator as parameters. FIGS. 4A1 and 4A2 each show a case where the modulation rate of the speckle modulator is relatively slow, and $t_{mod}/2M_0 > t_{pw, ill}$. FIGS. 4B1 and 4B2 each show a case where the modulation rate of the speckle modulator is just $t_{mod}/2M_0 = t_{pw, ill}$. FIGS. 4C1 and 4C2 each show a case where the modulation rate of the speckle modulator is relatively fast, and $t_{mod}/M_0 = t_{pw, ill}$. In FIGS. 4A1 and 4A2, FIGS. 4B1 and 4B2, and FIGS. 4C1 and 4C2, the upper part shows a driving waveform of the speckle modulator with respect to elapsed time; the middle part shows, on a time axis, an irradiation waveform of the illumination pulse generator; and the lower part shows an effective amplitude modulation factor $M_{eff}$ serving as an indicator of the speckle reduction effect and the speckle reduction effect, with respect to the irradiation timing of the illumination pulse generator. Here, FIGS. 4A1, 4B1, and 4C1 each show a case where the amplitude modulation factor $M_0$ of the speckle modulator is 1 ($M_0=1$), and FIGS. 4A2, 4B2, and 4C2 each show a case where the amplitude modulation factor $M_0$ of the speckle modulator is $2>1$ ($M_0=2>1$). In FIGS. 4A1 and 4A2, FIGS. 4B1 and 4B2, and FIGS. 4C1 and 4C2, a numerical value of the speckle reduction effect is indicated after being standardized in a speckle contrast in which the numerical value is proportional to an inverse number of the speckle contrast, and the speckle reduction effect brought about by the speckle modulator is at its greatest. For this reason, the numerical value of the speckle reduction effect is plotted so as to be 1 under the condition that the reduction effect brought about by the speckle modulator is saturated and reaches a maximum.

The summary of what can be seen from FIGS. 4A1 and 4A2, FIGS. 4B1 and 4B2, and FIGS. 4C1 and 4C2 is as follows.

Even in the case of $t_{mod} > 2M_0 t_{pw, ill}$, the speckle reduction effect can be most efficiently extracted by synchronizing the speckle modulator and the illumination light generator. However, in the case of $M_{eff} < 1$, it is impossible to reduce the speckle reduction effect to the extent that the speckle reduction effect is saturated.

Even if the speckle modulator is not driven at a high speed so that $t_{mod} < 2t_{pw, ill}$ by driving the speckle modulator with $M_0 \geq 1$, the effect of the maximum level at which the speckle reduction effect is saturated can be extracted by synchronizing the speckle modulator and the illumination pulse generator even under the condition that the driving speed is $M_0$ times slower than $t_{mod} < 2t_{pw, ill}$ (i.e., even under the condition that $t_{mod} \leq 2M_0 t_{pw, ill}$).

When the speckle modulator is driven at $M_0 \geq 1$ and further, in the case of $t_{mod} \leq M_0 t_{pw, ill}$, the speckle reduction effect can be stably brought to a value close to a maximum value without much dependence on the timing of the synchronization control.

In the conventional idea, which does not take into account the concept of the amplitude modulation factor $M_0$, it is considered that the speckle reduction effect cannot be maximized and achieved without temporal variation unless $t_{mod} < t_{pw, ill}$; however, even if the modulation rate of the speckle modulator is decreased by $M_0$ times (or even if the pulse emission period is shortened by $M_0$ times), the speckle reduction effect can be stabilized and maximized.

As described above, in an illumination device, the driving period $t_{mod}$ and the drive timing of a speckle modulator greatly influence the speckle reduction effect, depending on the pulse emission period $t_{pw, ill}$ and/or the illumination timing. Similarly, in an imaging system having an imager, the driving period $t_{mod}$ and the drive timing of a speckle modulator greatly influence the speckle reduction effect, depending on the exposure period $t_{pw, exp}$ and/or the exposure timing.

Therefore, in the following embodiments, all pulse emission periods may be replaced with any of a pulse emission period or an exposure period $t_{pw, exp}$ of the imager or an overlapping portion of them.

First Embodiment

FIG. 5 schematically shows the overall configuration of an endoscope system including an imaging system according to a first embodiment.

An endoscope system 300 includes an endoscope scope 310 and an endoscope controller 320. The endoscope scope 310 and the endoscope controller 320 are connected by a scope connector 312 and a controller connector 322.

An imaging system 100 according to the present embodiment includes an illuminating device 102 configured to illuminate an observation object 190 and an imaging device 104 configured to perform imaging of the observation object 190 illuminated by the illuminating device 102.

In FIG. 5, the scope connector 312 and the controller connector 322 configured to connect the endoscope scope 310 and the endoscope controller 320 are depicted as one piece, but the endoscope scope 310 side of the illuminating device 102 and the endoscope controller 320 side thereof, and the endoscope scope 310 side of the imaging device 104 and the endoscope controller 320 side thereof may be respectively connected by separate connectors.

The illuminating device 102 includes an illumination light generator 110 configured to generate illumination light of coherent light, a light guide optical system 120 configured to guide coherent light emitted from the illumination light generator 110, and a light distributing optical system 140 configured to control the light distribution of the coherent light guided by the light guide optical system 120 and to emit the light.

The illumination light generator 110 includes a laser light source 112 configured to emit laser light as coherent light, and a driver 114 configured to drive the laser light source 112. For example, the illumination light generator 110 is composed of an illumination pulse generator configured to generate illumination pulses of coherent light during a predetermined pulse emission period $t_{pw, ill}$. In the following description, it is assumed that the illumination light generator 110 is composed of an illumination pulse generator unless otherwise specified.

The light guide optical system 120 includes a first optical fiber 124 and a second optical fiber 130 as light guides for guiding coherent light. The light guide is not limited to an optical fiber, and instead, a flexible waveguide may be used, for example. The light guide optical system 120 also includes a first fiber coupling lens 122 configured to couple coherent light emitted from the laser light source 112 to the optical fiber 124, a collimating lens 126 configured to collimate a light beam emitted from the first optical fiber 124, and a second fiber coupling lens 128 configured to couple the light beam collimated by the collimating lens 126 to the second optical fiber 130. Although the first fiber coupling lens 122, the collimating lens 126, and the second fiber coupling lens 128 are each schematically depicted as one lens in FIG. 5, in practice they may be composed of a single lens or a plurality of lenses.

The imaging device 104 includes an imager 150 configured to perform imaging of an image within a predetermined exposure period $t_{pw, exp}$, an image processing circuit 160 configured to perform necessary image processing on image information acquired by the imager 150, and a display 170 configured to display an image processed by the image processing circuit 160.

Laser light emitted from the laser light source 112 is converged by the first fiber coupling lens 122, enters the first optical fiber 124, and is guided by the first optical fiber 124. A beam of the laser light emitted from the first optical fiber 124 is converted into a parallel light beam by the collimating lens 126, before propagating in the space, is then converged by the second fiber coupling lens 128, enters the second optical fiber 130, and is guided by the second optical fiber 130. The laser light guided by the light guide optical system 120 is emitted after the light distribution is controlled by the light distributing optical system 140. Light L1 emitted from the light distributing optical system 140 is applied to the observation object 190.

The light L1 applied to an observation object 190 is reflected, diffracted, scattered, etc. by the observation object 190. Part L2 of the light reflected, diffracted, scattered, etc. by the observation object 190 enters the imager 150. The imager 150 acquires image information on the observation object 190 based on the light L2 received from the observation object 190. The image information acquired by the imager 150 is displayed on the display 170 after being subjected to image processing by the image processing circuit 160.

In an imaging system using coherent light, if the observation object has a scattering structure, such as a subtle unevenness (concavo-convex), speckle occurs on the imaging surface of the imager and appears as speckle noise in an acquired image. Since this phenomenon is not limited to electronic imaging systems, but also occurs on the retina of a living body corresponding to an imaging surface, the same problem occurs in an illuminating device using coherent light. The cause of speckle is that light scattered from the unevenness (concavo-convex), etc. of an observation object interferes, and a fine light-dark pattern is formed on the imaging surface or the retina.

In order to reduce the speckle noise, the illuminating device 102 includes a speckle modulator 200 configured to modulate speckle caused by coherent light.

The speckle modulator 200 may be composed of, for example, a light guide characteristic modulator configured to change the optical characteristics of coherent light guided by the light guide optical system 120. Or, the speckle modulator 200 may be composed of a wavelength modulator configured to change the optical characteristics of coherent light.

For example, the light guide characteristic modulator may be composed of a phase modulator configured to temporally change the phase of coherent light guided by the light guide optical system 120. For example, the phase modulator may be composed of a light guide variation device configured to apply mechanical change to the light guide included in the light guide optical system 120 configured to guide coherent light. The mechanical change applied to the light guide may be, for example, vibration, rotation, or twist. Alternatively, the phase modulator may be composed of a refractive index modulator configured to temporally change the refractive index of a part of the light guide optical system 120 configured to guide coherent light. The refractive index modulator may include, for example, an electro-optic element or an acousto-optic element. The phase modulator may also have a concavo-convex plate with protrusions and recesses greater than 1/10 the wavelength of the coherent light, for example. Alternatively, the phase modulator may be composed of a wavelength modulator configured to temporally change the wavelength of coherent light emitted from the illumination light generator 110.

In the present embodiment, the speckle modulator 200 includes a first light guide characteristic modulator 210 disposed in a middle part between both ends of the first optical fiber 124, and a second light guide characteristic modulator 220 disposed on the optical path of the collimated light beam between the collimating lens 126 and the second fiber coupling lens 128. The speckle modulator 200 also includes a wavelength modulator 230 configured to temporally change the wavelength of laser light emitted from the laser light source 112.

The wavelength modulator 230 includes a wavelength-variable laser light source 112 and a wavelength modulation circuit 232 configured to control the laser light source 112 so as to temporally change the wavelength of the laser light emitted from the laser light source 112. The configurations of the first light guide characteristic modulator 210 and the second light guide characteristic modulator 220 will be described later with reference to FIGS. 6A to 6D.

The speckle modulator 200 need not necessarily include all of the first light guide characteristic modulator 210, the second light guide characteristic modulator 220, and the wavelength modulator 230, and simply need inclusions of at least one of them.

The illuminating device 102 also includes a synchronization controller 240 configured to control the illumination light generator 110 and the speckle modulator 200 so as to synchronize the pulse generation timing of the illumination light generator 110 and the drive timing of the speckle modulator 200. For example, the synchronization controller 240 controls the illumination light generator 110 and the speckle modulator 200 so as to synchronize the pulse generation timing of the illumination light generator 110 and the drive timing of the first light guide characteristic modulator 210 and/or the second light guide modulator 220. Furthermore, the synchronization controller 240 may also control the illumination light generator 110, the speckle modulator 200, and the imager 150 so as to synchronize the pulse generation timing of the illumination light generator 110, the drive timing of the speckle modulator 200, and the imaging timing of the imager 150.

The synchronization controller 240 is provided in order to sufficiently extract the speckle reduction effect by optimizing the drive timing of the speckle modulator 200, the illumination timing, and the imaging timing to increase $M_{eff}$, even if there are restrictions on the driving intensity amplitude $I_{mod,\ 0}$ of the speckle modulator 200 and the pulse emission period $t_{pw,\ ill}$ of the illumination light generator 110.

Here, the illumination timing means temporal timing of the pulse emission period generated by the illumination light generator 110, and the imaging timing means light-receiving timing of the imager 150 within one imaging frame.

As a method of performing the synchronization control for optimizing the imaging timing, the illumination timing, and the drive timing of the speckle modulator described above, the following various synchronization methods may be used: 1) a method in which the imaging timing is used as the master time, and the illumination timing and the drive timing of the speckle modulator are synchronized with the master time at predetermined timing; 2) a method in which the illumination timing is used as the master time, and the imaging timing and the drive timing of the speckle modulator are synchronized with the master time at predetermined timing; 3) a method in which the drive timing of the speckle modulator is used as the master time, and the imaging timing and the illumination timing are synchronized with the master time at predetermined timing; 4) a method in which a system clock of an illuminating device or an imaging system is used as the master time, and the imaging timing, the illumination timing, and the drive timing of the speckle modulator are synchronized with the master time, etc.

Furthermore, on the condition that these periods can all be synchronized, an imaging period (frame rate) $1/f_r$, an illumination pulse generation period $t_p$, and a driving period $t_{mod}$ of the speckle modulator are not necessarily the same. These periods are applicable even if they have a relationship of an integer multiple; for example, these periods may be expressed as $1/f_r=2n \cdot tp=^2 n \cdot t_{mod}$, or $t_p=2n \cdot t_{mod}$, where n is a natural number. (The case of generating a plurality of illumination pulses in one frame will be described in the second embodiment.)

In the second embodiment, an imaging system is considered, and it is assumed that a plurality of illumination pulses are distributed within $t_{on}$; however, a desired effect can be obtained even in an illuminating device including no imager (an illuminating device for observation with naked eye), by division of a plurality of pulses. In this case, an effective pulse emission period $t_{pw,\ eff}$ can be defined as a period from the start point of the next illumination pulse with the widest pulse interval to the end point of the last illumination pulse.

In other words, the effective pulse emission period $t_{pw,\,eff}$ can be said to be a period from the lighting time of the first illumination pulse to the extinction time of the last illumination pulse, in one illumination pulse group.

Figure 6C:
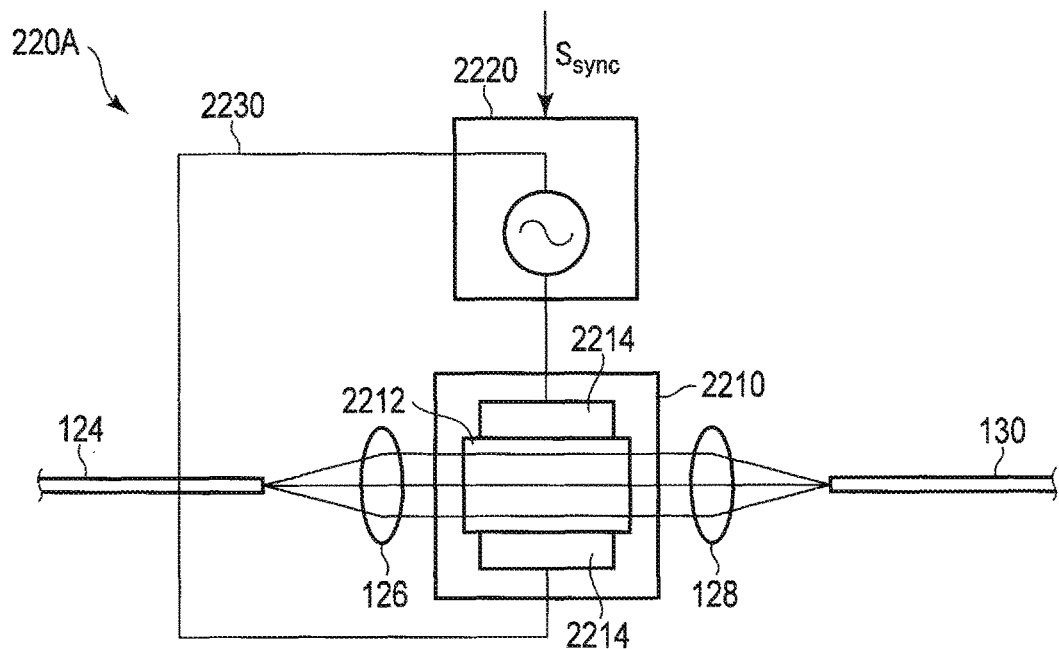
FIG. 6C schematically shows the configuration of a light guide characteristic modulator configured to change the optical characteristic of laser light by changing a refractive index of the optical path between a collimating lens and a second fiber coupling lens.
Figure 6D:
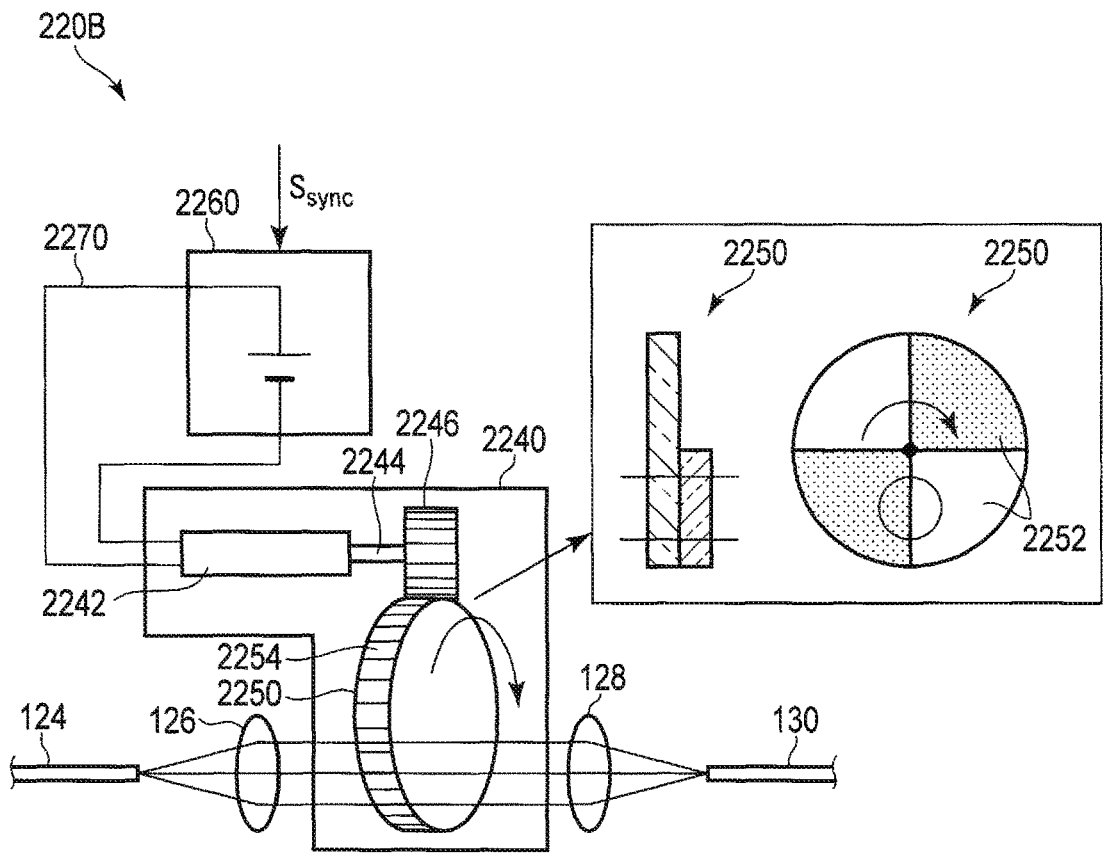
FIG. 6D schematically shows the configuration of a light guide characteristic modulator configured to change the optical characteristic of the laser light by changing an optical path length of the optical path between a collimating lens and a second fiber coupling lens.

FIGS. 6A, 6B, 6C, and 6D each show a configuration example of a light guide characteristic modulator that functions as a speckle modulator. Among these, FIGS. 6A and 6B show a configuration example of the first light guide characteristic modulator 210 disposed in a middle position of an optical fiber, and FIGS. 6C and 6D show a configuration example of the second light guide characteristic modulator 220 disposed on the optical path between the collimating lens 126 and the second fiber coupling lens 128.

FIG. 6A schematically shows a configuration of a light guide characteristic modulator 210A configured to change the optical characteristics of laser light guided by the first optical fiber 124, by vibrating the first optical fiber 124.

The light guide characteristic modulator 210A includes a light guide variation device 2110 configured to apply mechanical change to the first optical fiber 124 configured to guide laser light, and a driver 2130 configured to drive the light guide variation device 2110. Here, the light guide variation device 2110 is an optical fiber vibration device configured to apply vibration to the first optical fiber 124. The light guide variation device 2110 has a vibration motor 2112. The vibration motor 2112 is placed on a damper 2118 configured to absorb vibration. The damper 2118 is placed on a fixing member (not shown). A weight 2116 having a center of gravity asymmetric with respect to a rotation axis 2114 is attached to the rotation axis 2114 of the vibration motor 2112. An abutting member 2120 is fixed to the vibration motor 2112. The abutting member 2120 is in contact with the first optical fiber 124.

When the vibration motor 2112 is supplied with current from the driver 2130 through an electrical wire 2140, the rotation axis 2114 rotates. Since a weight 2116 having an asymmetric center of gravity is attached to the rotation axis 2114, the vibration motor 2112 vibrates when the rotation axis 2114 rotates. The vibration is transmitted to the optical fiber 124 through then abutting member 2120. As a result, the first optical fiber 124 is vibrated. With this configuration, the bending of the first optical fiber 124 changes periodically, so that the phase or the mode of the laser light guided by the first optical fiber 124 is temporally changed.

In the light guide characteristic modulator 210A, preferably, the driving intensity amplitude $I_{mod,\,0}$ of the light guide characteristic modulator 210A is 5Φc or more in terms of displacement of vibration of the first optical fiber 124 caused by the light guide variation device 2110, where Φc is a core diameter of the first optical fiber 124.

The centrifugal force of the light guide characteristic modulator 210A is increased by increasing the rotational speed of the vibration motor 2112. By utilizing this effect, the driving intensity amplitude $I_{mod,\,0}$ of the light guide characteristic modulator 210A can be increased by increasing the vibration amplitude $X_{mod,\,0}$, etc. Alternatively, if the weight 2116 is attached around the rotation axis 2114 of the vibration motor 2112 through an elastic member, the light guide characteristic modulator 210A is configured so that the asymmetry of the center of gravity of the weight 2116 with respect to the rotation axis 2114 increases as the rotational speed of the vibration motor 2112 increases. For this reason, when the rotational speed of the vibration motor 2112 is increased, the vibration amplitude further increases.

FIG. 6B schematically shows the configuration of a light guide characteristic modulator 210B configured to change the optical characteristics of laser light guided by the first optical fiber 124 by rotating the first optical fiber 124.

The light guide characteristic modulator 210B includes a light guide variation device 2150 configured to apply mechanical change to the first optical fiber 124 configured to guide laser light, and a driver 2170 configured to drive the light guide variation device 2150. Here, the light guide variation device 2150 is an optical fiber rotation device configured to apply reciprocal rotation to the first optical fiber 124. The light guide variation device 2150 has a rotation motor 2152. The rotation motor 2152 is placed on a fixing member (not shown). A gear 2156 is attached to a rotation axis 2154 of the rotation motor 2152. The gear 2156 engages with a gear 2158 fixed on the first optical fiber 124.

When the rotation motor 2152 is supplied with current from a driver 2170 through an electrical wire 2180, the rotation axis 2154 periodically rotates clockwise and counterclockwise reciprocally within a predetermined angle range. The reciprocating rotational motion is transmitted to the gear 2158 fixed on the first optical fiber 124 through the gear 2156. As a result, the first optical fiber 124 is reciprocally rotated. With this configuration, the twist around the axis of the first optical fiber 124 changes periodically, so that the phase or the mode of the laser light guided by the first optical fiber 124 is temporally changed.

In the light guide characteristic modulator 210B, the driving intensity amplitude $I_{mod,\,0}$ of the light guide characteristic modulator 210B is preferably 10° or more in terms of an angle at which the first optical fiber 124 is twisted.

The driving intensity amplitude $I_{mod,\,0}$ of the light guide characteristic modulator 210B can be increased, for example, by increasing the angle of the reciprocal rotation of the rotation motor 2152 to increase a torsion amplitude $\theta_{mod,\,0}$.

FIG. 6C schematically shows the configuration of a light guide characteristic modulator 220A configured to change the optical characteristics of laser light by changing the refractive index of an optical path between the collimating lens 126 and the second fiber coupling lens 128.

The light guide characteristic modulator 220A includes a refractive index modulator 2210 disposed on the optical path between the collimating lens 126 and the second fiber coupling lens 128, and a driver 2220 configured to drive the refractive index modulator 2210. The refractive index modulator 2210 is an optical element configured to temporally change the refractive index of an optical path of laser light passing through the refractive index modulator 2210. The refractive index modulator 2210 may be composed of, for example, an electro-optic element. Alternatively, the refractive index modulator 2210 may be composed of an acousto-optic element, for example. The refractive index modulator 2210 includes an optical medium 2212 configured to transmit laser light, and a driving electrode 2214 provided on the optical medium 2212.

In the refractive index modulator 2210, when an alternating-current voltage is applied from the driver 2220 to the driving electrode 2214 through an electrical wire 2230, the refractive index of the optical medium 2212 periodically and temporally changes. As a result, a phase of the laser light passing through the optical medium 2212 is temporally changed.

In the light guide characteristic modulator 220A, the driving intensity amplitude $I_{mod,\,0}$ of the light guide characteristic modulator 220A is preferably $\Delta n/n \geq \lambda c/Lm$ in terms of a change in the refractive index of the refractive index modulator 2210, where Lm is the length of the refractive index modulator 2210 in the light guide direction, Δn/n is a change in refractive index, and λc is is a center wavelength of a spectrum of an illumination pulse.

The driving intensity amplitude $I_{mod,\,0}$ of the light guide characteristic modulator 220A can be controlled by the magnitude of the voltage applied to the refractive index modulator 2210.

FIG. 6D schematically shows the configuration of a light guide characteristic modulator 220B configured to change the optical characteristics of laser light by changing the optical path length of an optical path between the collimating lens 126 and the second fiber coupling lens 128.

The light guide characteristic modulator 220B includes a refractive index modulator 2240 disposed on the optical path between the collimating lens 126 and the second fiber coupling lens 128, and a driver 2260 configured to drive the refractive index modulator 2240. The refractive index modulator 2240 has a phase difference disc 2250 disposed on the optical path. The phase difference disc 2250 has a concavo-convex pattern 2252 with protrusions and recesses greater than 1/10 the wavelength of a laser beam. The phase difference disc 2250 is supported so as to be rotatable around the axis out of the optical path. A gear 2254 is formed on the outer periphery of the phase difference disc 2250. The refractive index modulator 2240 also has a rotation motor 2242 configured to rotate the phase difference disc 2250. The rotation motor 2242 is placed on a fixing member (not shown). A gear 2246 is attached to a rotation axis 2244 of the rotation motor 2242. The gear 2246 engages with the gear 2254 of the phase difference disc 2250.

When the rotation motor 2242 is supplied with current from a driver 2260 through an electric wire 2270, the rotation axis 2244 is rotated. The rotational motion is transmitted to the gear 2254 formed on the phase difference disc 2250 through the gear 2246. As a result, the phase difference disc 2250 is rotated, and a concave-convex pattern 2252 is moved across the optical path. With this configuration, the optical path length of the laser light passing through the phase difference disc 2250 periodically changes, so that the phase of the laser light is temporally changed.

The driving intensity amplitude $I_{mod,\,0}$ of the light guide characteristic modulator 220B can be increased by increasing the voltage applied to the rotation motor 2242 to increase the rotation speed.

In the imaging system 100 shown in FIG. 5, when any one of the light guide characteristic modulators 210A, 210B, 220A, and 220B shown in FIGS. 6A to 6D is mounted as the speckle modulator 200, the behavior and the effect of the speckle modulator 200 are as follows, as described with reference to FIGS. 1A to 1C, 2A to 2C, and 3A1 to 3C2.

As the change width $\Delta I_{mod}$ of the driving intensity of the speckle modulator 200 is increased, the speckle reduction effect increases until $\Delta I_{mod}$ becomes $\Delta I_{mod,\,th}$, and saturates in the vicinity where $\Delta I_{mod}$ becomes $\Delta I_{mod,\,th}$.

It is considered that when the effective amplitude modulation factor $M_{eff}$ is increased (by increasing the change width $\Delta I_{mod}$ of the driving intensity of the speckle modulator 200), the speckle reduction effect also increases together with $M_{eff}$, and the speckle reduction effect is substantially saturated when $M_{eff} > 1$, where an effective amplitude modulation factor $M_{eff}$ is a value obtained by standardizing a change width $\Delta I_{mod}$ of the driving intensity of the speckle modulator 200 with $\Delta I_{mod,\,th}$.

Also,

When the driving amplitude or driving width of the speckle modulator 200 is increased so as to increase $M_0$ or $M_{eff}$, the speckle reduction effect is increased.

For this reason, when the speckle modulator 200 and the illumination light generator 110 are synchronized so as to increase the change width $\Delta I_{mod}$ of the driving intensity of the speckle modulator 200, the speckle reduction effect reaches a maximum.

When the imaging timing, the illumination timing, and the modulation timing are optimized by setting $M_{eff} \geq 1$, the speckle reduction effect can be increased to a maximum. Furthermore, under the condition of $M_{eff} \geq 1$, a stable speckle reduction effect is obtained in which the speckle reduction effect is saturated with small timing dependency of imaging, illumination, and modulation.

In addition, as described with reference to FIGS. 4A1 to 4C2, with respect to the driving period $t_{mod}$, the pulse emission period $t_{pw,\,ill}$, and the amplitude modulation factor $M_0$ of the speckle modulator, the speckle reduction effect result is as follows.

Even in the case of $t_{mod} > 2M_0 t_{pw,\,ill}$, the speckle reduction effect can be most efficiently extracted by synchronizing the speckle modulator 200 and the illumination light generator 110. However, in the case of $M_{eff} < 1$, it is impossible to reduce the speckle reduction effect to the extent that the speckle reduction effect is saturated.

Even if the speckle modulator 200 is not driven at a high speed so that $t_{mod} < 2t_{pw,\,ill}$ by driving the speckle modulator 200 with $M_0 \geq 1$, the effect of the maximum level at which the speckle reduction effect is saturated can be extracted by synchronizing the speckle modulator 200 and the illumination pulse generator 110 even under the condition that the driving speed is $M_0$ times slower than $t_{mod} < 2t_{pw,\,ill}$ (i.e., even under the condition that $t_{mod}\,2M_0 t_{pw,\,ill}$).

When the speckle modulator 200 is driven at $M_0 \geq 1$ and further, in the case of $t_{mod} \leq M_0 t_{pw,\,ill}$, the speckle reduction effect can be stably brought to a value close to a maximum value without much dependence on the timing of the synchronization control.

As described above, the imaging system 100 according to the present embodiment can control the light quantity by using PWM based on the pulse emission period $t_{pw,\,ill}$ of the illumination light generator 110, and can also control the light quantity by using PWM based on $t_{pw,\,exp}$ of the imager 150.

When controlling the light quantity by using PWM based on the pulse emission period $t_{pw,\,ill}$ of the illumination light generator 110, the imaging system 100 of the present embodiment operates as follows.

The synchronization controller 240 controls the speckle modulator 200 so as to operate at least during a pulse emission period $t_{pw,\,ill}$ per illumination pulse.

The speckle modulator 200 periodically changes the driving intensity $I_{mod}$ of the speckle modulator 200. The driving intensity amplitude $I_{mod,\,0}$ of the speckle modulator 200 is preferably set to be equal to or greater than a driving intensity threshold width $\Delta I_{mod,\,th}$. For example, the driving intensity amplitude $I_{mod,\,0}$ of the speckle modulator 200 is set so that the change width $\Delta I_{mod}$ of the driving intensity of the speckle modulator 200 during the pulse emission period $t_{pw,\,ill}$ is a value equal to or greater than the driving intensity threshold width $\Delta I_{mod,\,th}$.

Furthermore, in order to enhance the speckle reduction effect, the synchronization controller 240 controls the illumination light generator 110 and the speckle modulator 200 so as to synchronize at least the pulse generation timing of the illumination light generator 110 and the drive timing of the speckle modulator 200 as follows.

The synchronization controller 240 controls the illumination light generator 110 so as to generate illumination pulses during an exposure period $t_{pw,\ exp}$ of the imager 150.

When the pulse emission period $t_{pw,\ th}$ is a period shorter than ½ of the speckle modulation period $t_{mod}$, the synchronization controller 240 controls the illumination light generator 110 and the speckle modulator 200 so that the pulse emission period $t_{pw,\ ill}$ includes the time at which the change rate of the driving intensity $I_{mod}$ of the speckle modulator 200 substantially reaches a maximum. For example, the synchronization controller 240 controls the illumination light generator 110 and the speckle modulator 200 so that the center of the pulse emission period $t_{pw,\ ill}$ is the time at which the change rate of the driving intensity $I_{mod}$ of the speckle modulator 200 is substantially maximum. (Condition A)

Alternatively, when the pulse emission period $t_{pw,\ ill}$ is a period shorter than ½ of the speckle modulation period $t_{mod}$, the synchronization controller 240 controls the illumination light generator 110 and the speckle modulator 200 so that the pulse emission period $t_{pw,\ ill}$ includes neither a maximum value nor a minimum value of the driving intensity $I_{mod}$ of the speckle modulator 200. For example, the synchronization controller 240 controls the illumination light generator 110 and the speckle modulator 200 so that the pulse emission period $t_{pw,\ ill}$ includes the time at which the driving intensity $I_{mod}$ of the speckle modulator 200 takes a substantial center value between a maximum value and a minimum value. In particular, the synchronization controller 240 controls the illumination light generator 110 and the speckle modulator 200 so that the center of the pulse emission period $t_{pw,\ ill}$ is the time at which the driving intensity $I_{mod}$ of the speckle modulator 200 takes a substantial center value between a maximum value and a minimum value. (Condition B)

When the pulse emission period $t_{pw,\ ill}$ is a period equal to or longer than ½ of the speckle modulation period $t_{mod}$, the synchronization controller 240 controls the illumination light generator 110 and the speckle modulator 200 so that the pulse emission period $t_{pw,\ ill}$ includes the time at which the driving intensity $I_{mod}$ of the speckle modulator 200 takes a maximum value and the time at which the driving intensity $I_{mod}$ of the speckle modulator 200 takes a minimum value. (Condition C)

There may be one or more illumination pulses with different time delays synchronized with the speckle modulator 200. When the pulse emission period is shorter than ½ of the speckle modulation period $t_{mod}$, it is more preferable to satisfy (Condition A) or (Condition B). For example, when a second illumination pulse comes exactly half a period after the first illumination pulse, if the first illumination pulse includes the time at which the slope (absolute value) of the driving intensity $I_{mod}$ of the speckle modulator 200 is at a maximum, the second illumination pulse also includes the time at which the slope (absolute value) of the driving intensity $I_{mod}$ of the speckle modulator 200 reaches its maximum (see FIG. 3B1). In the case where the pulse emission period is equal to or longer than ½ of $t_{mod}$, it is more preferable to satisfy (Condition C).

Furthermore, the synchronization controller 240 controls the illumination pulse generator 110, the speckle modulator 200, and the imager 150 so as to synchronize the pulse generation timing of the illumination light generator 110, the drive timing of the speckle modulator 200, and the imaging timing of the imager 150. The synchronization controller 240 drives the speckle modulator 200 and the illumination light generator 110 with $M_0 \geq 1$. Furthermore, the synchronization controller 240 drives the speckle modulator 200 and the illumination light generator 110 with $t_{mod} \leq 2M_0 t_{pw,\ ill}$. Alternatively, the synchronization controller 240 drives the speckle modulator 200 and the illumination light generator 110 with $t_{pw,\ ill} < t_{mod} \leq M_0 t_{pw,\ ill}$.

The above description is an explanation of operations in the case where the light quantity is controlled by using PWM based on a pulse emission period $t_{pw,\ ill}$ of the illumination light generator 110. However, when the light quantity is controlled by using PWM based on $t_{pw,\ exp}$ of the imager 150, the imaging system 100 of the present embodiment instead operates as follows. In this case, the illumination light generator 110 need not necessarily be composed of an illumination pulse generator configured to generate illumination pulses during a predetermined pulse emission period $t_{pw,\ ill}$ of coherent light.

The synchronization controller 240 controls the speckle modulator 200 so as to operate at least during the exposure period $t_{pw,\ exp}$.

The speckle modulator 200 periodically changes the driving intensity $I_{mod}$ of the speckle modulator. The driving intensity amplitude $I_{mod,\ 0}$ of the speckle modulator 200 is set to be equal to or greater than a driving intensity threshold width $\Delta I_{mod,\ th}$. For example, the driving intensity amplitude $I_{mod,\ 0}$ of the speckle modulator 200 is set so that the change width $\Delta I_{mod}$ of the driving intensity of the speckle modulator 200 during the exposure period $t_{pw,\ exp}$ is equal to or greater than the driving intensity threshold width $\Delta I_{mod,\ th}$.

In order to enhance the speckle reduction effect, the synchronization controller 240 controls at least the imager 150 and the speckle modulator 200 in synchronization as follows.

When the exposure period $t_{pw,\ exp}$ is a period shorter than ½ of the speckle modulation period $t_{mod}$, the synchronization controller 240 controls the imager 150 and the speckle modulator 200 so that the exposure period $t_{pw,\ exp}$ includes the time at which the change rate of the driving intensity $I_{mod}$ of the speckle modulator 200 substantially reaches a maximum. For example, the synchronization controller 240 controls the imager 150 and the speckle modulator 200 so that the center of the exposure period $t_{pw,\ exp}$ is the time at which the change rate of the driving intensity $I_{mod}$ of the speckle modulator 200 becomes substantially maximum.

Alternatively, when the exposure period $t_{pw,\ exp}$ is a period shorter than ½ of the speckle modulation period $t_{mod}$, the synchronization controller 240 controls the imager 150 and the speckle modulator 200 so that the exposure period $t_{pw,\ exp}$ include neither a maximum value nor a minimum value of the driving intensity $I_{mod}$ of the speckle modulator 200. For example, the synchronization controller 240 controls the imager 150 and the speckle modulator 200 so that the exposure period $t_{pw,\ exp}$ includes the time at which the driving intensity $I_{mod}$ of the speckle modulator 200 takes a substantial center value between a maximum value and a minimum value. In particular, the synchronization controller 240 controls the imager 150 and the speckle modulator 200 so that the center of the exposure period $t_{pw,\ exp}$ is the time at which the driving intensity $I_{mod}$ of the speckle modulator 200 takes a substantial center value between a maximum value and a minimum value.

When the exposure period $t_{pw,\ exp}$ is equal to or longer than ½ of the speckle modulation period $t_{mod}$, the synchronization controller 240 controls the imager 150 and the speckle modulator 200 so that the exposure period $t_{pw,\ exp}$ includes the time at which the driving intensity $I_{mod}$ of the speckle modulator 200 takes a maximum value and the time at which the driving intensity $I_{mod}$ of the speckle modulator 200 takes a minimum value.

In the imaging system 100 of the present embodiment, speckle noise can be reduced stably and effectively by the operations of the above-described configuration. In addition, it is also possible to add a configuration for reducing speckle noise stably and effectively to an existing illuminating device or imaging system without incurring a large cost. It is possible to sufficiently extract the speckle reduction effect by optimizing the drive timing of the speckle modulator 200, the illumination timing, and the imaging timing to increase $M_{eff}$, even if there are restrictions on the driving intensity amplitude $I_{mod, 0}$ of the speckle modulator 200 and the pulse emission period $t_{pw, ill}$ of the illumination light generator 110. Speckle noise can be reduced stably and efficiently for a short exposure period per imaging frame or a short pulse emission period per imaging frame required, in particular, when imaging is performed at a high imaging frame rate, when imaging is performed instantaneously in a short time, or when controlling light by a pulse width modulation (PWM) method.

In conventional imaging systems, it is predicted that a manner of reducing speckle by mechanically changing an optical fiber cannot satisfactorily exhibit the speckle pattern overlapping effect when the imaging frame rate is fast or when the imaging time is short. As a typical example, the exposure period $t_{pw, exp}$ per imaging frame of an imager is about $t_{pw, exp} \leq t_{on} = \frac{1}{2} \times \frac{1}{60}$ sec=8.3 msec, where an imaging frame rate $f_r$ of the imaging system is 60 fps, and about half of the time corresponding to an inverse number of the imaging frame rate is a possible exposure period $t_{on}$ per imaging frame of the imager; it is thereby considered that the shape or stress of the optical fiber needs to be changed at a period faster than the exposure period $t_{pw, exp}$. When an observation object needs to be exposed during the time shorter than the exposure period $t_{pw, exp}$ (when high-speed photographing is required), it is predicted that the effect of averaging due to overlapping of speckle patterns will be difficult to obtain due to restriction of mechanical vibration speed.

Furthermore, when the light quantity is controlled by pulse width modulation (PWM), which is frequently used in illuminating devices using laser light, the minimum value of the pulse emission period (or irradiation pulse width) $t_{pw, ill}$ of the light source is a period obtained by dividing the exposure period $t_{pw, exp}$ per imaging frame of the imager by the division number of the light control. For example, assuming a light control range of 30 dB, the minimum pulse emission period (or irradiation pulse width) $t_{pw, ill} (=t_{pw, exp})$ is approximately 8.3 msec/1000=8.3 μsec, but it seems difficult to achieve a mechanical vibration period corresponding to the minimum pulse emission period.

Furthermore, when viewed visually, a temporal response time of the eye can be regarded as an exposure period $t_{pw, exp}$ per imaging frame of an imager, and the speckle superposition needs to end within a time shorter than approximately 1/30 seconds (30 fps (frame/sec)). Furthermore, taking the light control by using PWM into account as a light controlling method of illumination, a more crucial request for the driving period of the mechanical vibration period arises for the same reason as described above.

In contrast, since the imaging system 100 of the present embodiment enables sufficient extraction of the speckle reduction effect by optimizing the drive timing of the speckle modulator 200, the illumination timing, and the imaging timing to increase the $M_{eff}$, it is possible to respond even to such a request. In other words, it is possible for the imaging system to reduce speckle noise stably and effectively for a short exposure period or a short pulse emission period required, in particular, when performing imaging at a high imaging frame rate, when performing imaging instantaneously in a short time, or when controlling light with a pulse width modulation (PWM) method.

Second Embodiment

Figure 7:
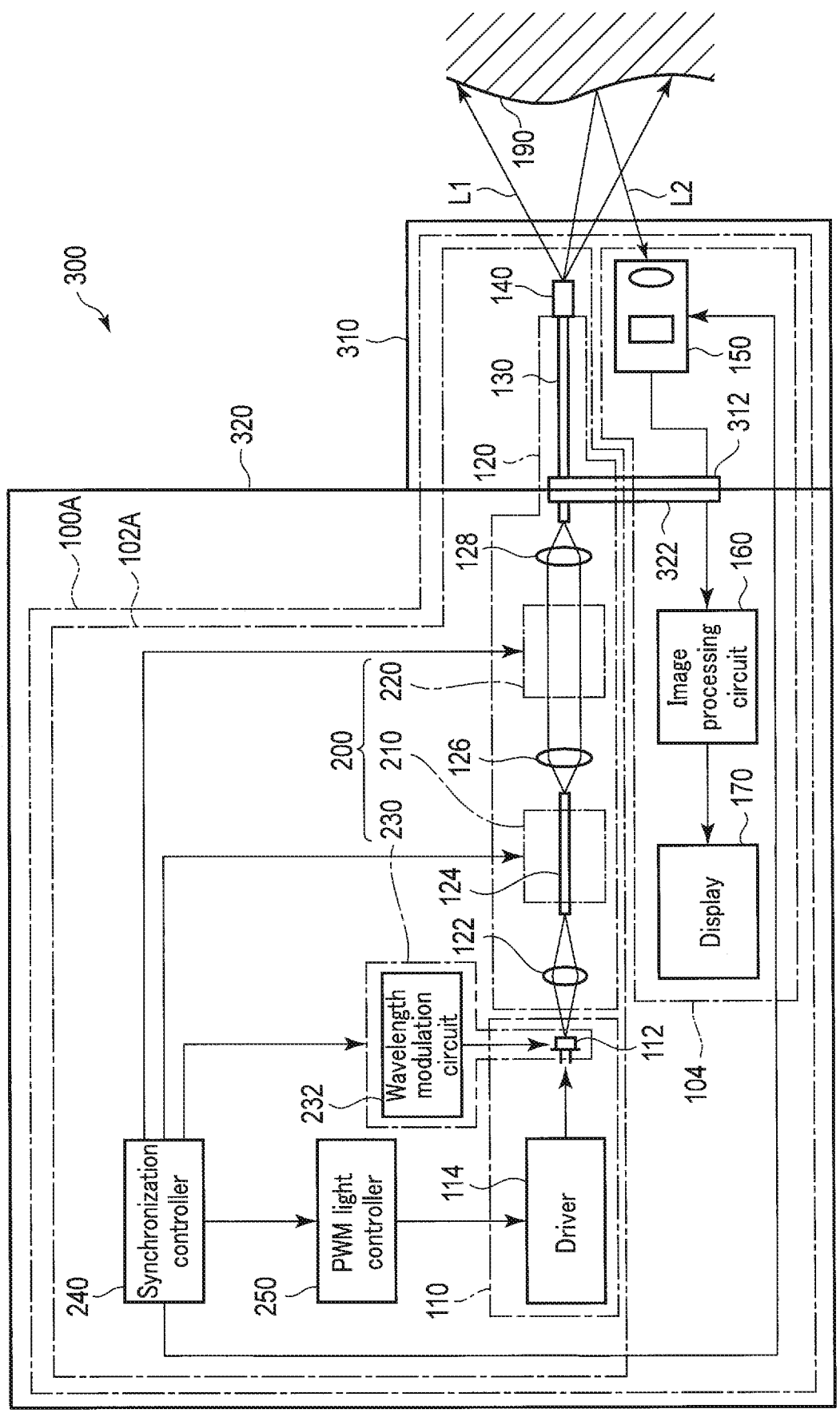
FIG. 7 schematically shows the overall configuration of an endoscope system including an imaging system according to a second embodiment.

FIG. 7 schematically shows the overall configuration of an endoscope system including an imaging system according to a second embodiment. In FIG. 7, members denoted by the same reference numerals as those shown in FIG. 5 are similar members, and detailed descriptions thereof are omitted. In the following, explanation will be given with emphasis on different parts. That is, the parts not touched upon by the following description are the same as those of the first embodiment.

The imaging system 100A according to the present embodiment is different from the imaging system 100 according to the first embodiment in an illuminating device 102A. In the illuminating device 102A, an illumination light generator 110 repeatedly generates an illumination pulse group including a plurality of illumination pulses, as an illumination pulse group sequence. For example, the number of the illumination pulses included in one illumination pulse group is 3 or more.

A period from the lighting time of the first lighting pulse to the extinction time of the last illumination pulse in one lighting pulse group is defined as an effective pulse emission period. At this time, the effective pulse emission period is, for example, a period that is equal to or longer than twice a net pulse emission period of a plurality of illumination pulses included in one illumination pulse group.

In order to control the illumination light generator 110 in this way, the illuminating device 102A includes a pulse width modulation (PWM) light controller 250. The pulse width modulation light controller 250 controls the effective illumination light quantity by controlling the pulse widths of a plurality of illumination pulses within an effective pulse emission period $t_{pw, eff}$. The pulse width modulation light controller 250 is a multiple-pulse-division-pulse width modulation system optical controller configured to divide a pulse emission period $t_{pw}$ corresponding to a desired light control quantity into a plurality of pulse emission periods $t_{pw}, t_{pw, ill, n}$ (n is a natural number of 2 or more). Here, n denotes the number of illumination pulses included in a single illumination pulse group. Furthermore, the pulse emission period $t_{pw, ill, i}$ (i=1, . . . , n) denotes the emission period of the i-th illumination pulse included in a single illumination pulse group.

In other words, the illuminating device 102A has a configuration in which a multiple pulse division type pulse-width modulation light controller 250 is added to the illuminating device 102 according to the first embodiment. The pulse width modulation light controller 250 controls a driver 114 of the illumination light generator 110 based on a signal input from a synchronization controller 240.

Figure 8A:
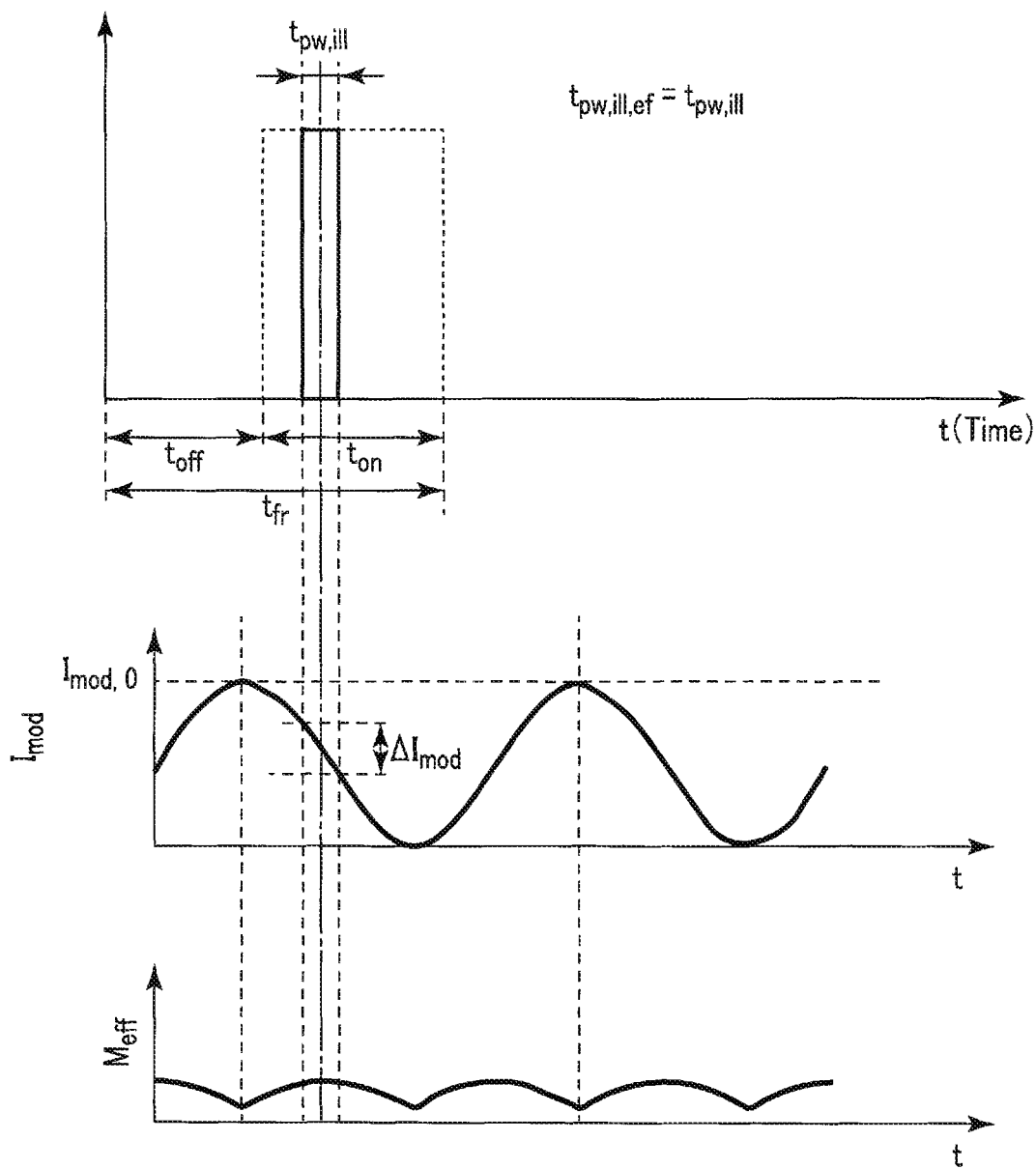
FIG. 8A shows an irradiation waveform of an illumination pulse generator, a driving waveform of a speckle modulator, and an effective amplitude modulation factor $M_{eff}$ serving as an indicator of speckle reduction effect, in a single pulse type pulse width modulation system.
Figure 8B:
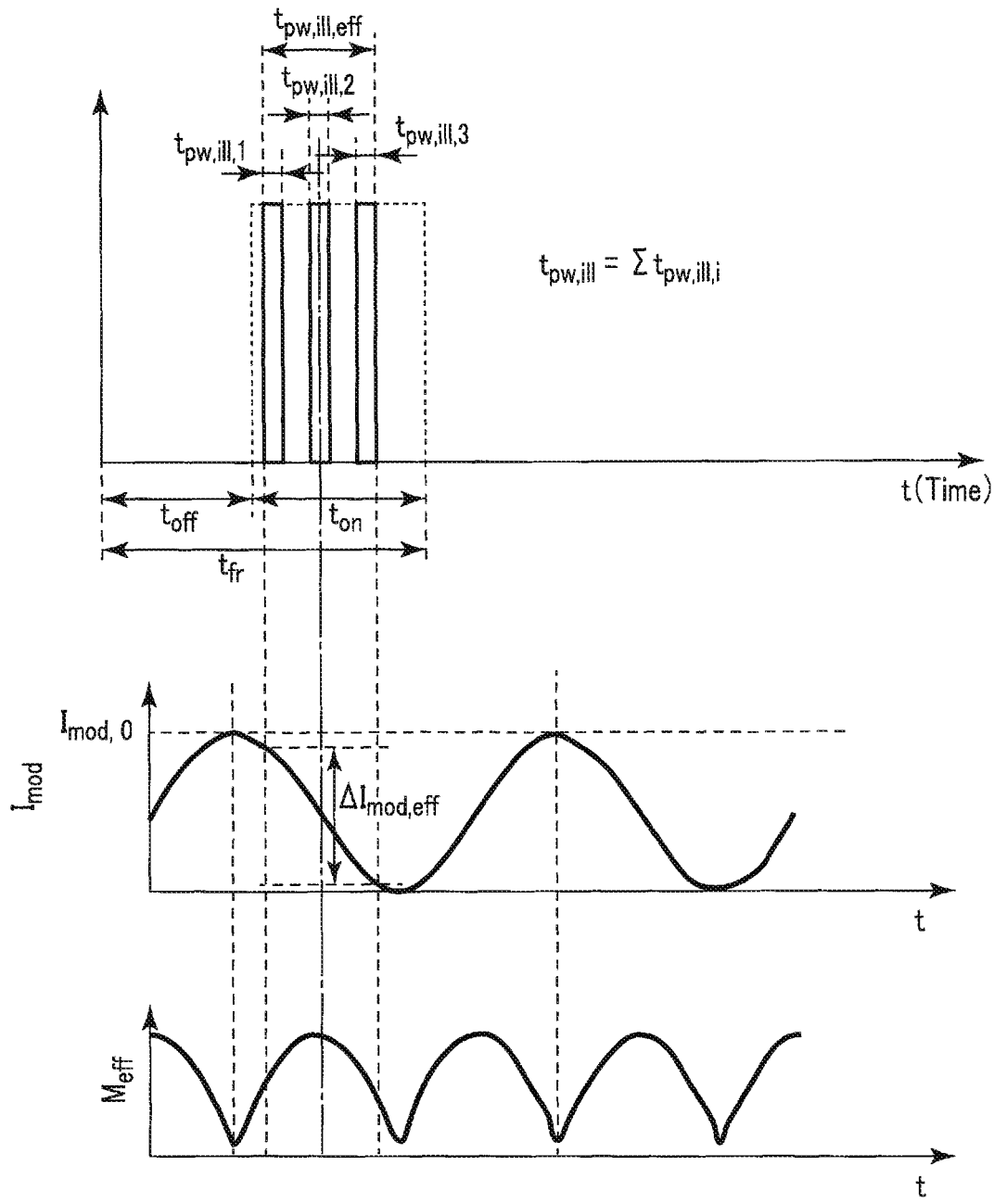
FIG. 8B shows an irradiation waveform of an illumination pulse generator, a driving waveform of a speckle modulator, and an effective amplitude modulation factor $M_{eff}$ serving as an indicator of speckle reduction effect, in a multi-pulse division type pulse width modulation system.

The "multiple pulse division type pulse-width modulation method" (FIG. 8B) will be described, while being compared with a well-known "single pulse type pulse-width modulation method" (FIG. 8A). FIGS. 8A and 8B show an irradiation waveform of the illumination pulse generator, a driving waveform of a speckle modulator, and an effective amplitude modulation factor $M_{eff}$ serving as an indicator of the speckle reduction effect in respective pulse width modulation systems.

A "single Pulse pulse-width modulation method" is, as shown in the upper part of FIG. 8A, a method of controlling the illumination light quantity so that the time width (or referred to as period) of an illumination pulse is a pulse emission period $t_{pw, ill}$ corresponding to a desired light quantity within a possible exposure period $t_{on}$.

On the other hand, as shown in the upper part of FIG. 8B, the "multiple pulse division type pulse width modulation method" proposed in the present application is a method of controlling the illumination light quantity by dividing the pulse emission period into a plurality of pulses so that $t_{pw, ill} = \Sigma t_{pw, ill, i}$.

As shown in the middle part of FIG. 8A and the middle part of FIG. 8B, even if the drive waveform of the speckle modulator is the same, in the "single pulse type pulse-width modulation method", $\Delta I_{mod}$ decreases in proportion to a decrease in the pulse emission period $t_{pw, ill}$ as shown in the lower part of FIG. 8A, thus leading to a decrease in $M_{eff}$. However, in the "multiple pulse division type pulse-width modulation method", even when the pulse emission period $t_{pw, ill}$ is made smaller by distributing the emission time of the illumination pulse in order to reduce the illumination light quantity, this leads to expansion of an effective pulse emission period. As a result, an effective $\Delta_{mod}$ (this is defined as $\Delta I_{mod, eff}$) can be expanded. For this reason, it is possible to effectively increase an effective amplitude modulation factor $M_{eff}$ serving as a speckle reduction indicator.

When the time width for passing a plurality of illumination pulses within the possible exposure period $t_{on}$ is regarded as an effective pulse emission period $t_{pw, eff}$, the "multiple pulse division pulse width modulation light controller" functions as an "effective pulse emission period expander" that effectively extends the pulse emission period. Here, the concept of "effective pulse emission period expander" is greater than the concept of "multiple pulse division type pulse width modulation light controller". This is because "effective pulse emission period expander" can expand the effective pulse emission period by temporally dividing an illumination pulse even when it is not for controlling the light quantity as described above.

When using an "effective pulse emission period expander" or "multiple pulse division type pulse width modulation light controller", it is preferable to set the time interval of an illumination pulse and the timing of the illumination pulse so that $\Delta I_{mod, eff}$ or $t_{pw, eff}$ is increased with respect to the synchronization controller 240.

An imaging system 100A of the present embodiment operates as follows.

The synchronization controller 240 controls the speckle modulator 200 so as to operate at least during an effective pulse emission period.

Furthermore, the synchronization controller 240 controls the illumination light generator 110, the speckle modulator 200, and the imager 150 so as to synchronize the pulse generation timing of the illumination light generator 110, the drive timing of the speckle modulator 200, and the imaging timing of the imager 150. For example, the synchronization controller 240 controls the illumination light generator 110 so as to generate illumination pulses within an exposure period ($t_{pw, exp}$) of the imager 150.

The speckle modulator 200 periodically changes the driving intensity $I_{mod}$ of the speckle modulator. The driving intensity amplitude $I_{mod, 0}$ of the speckle modulator 200 is preferably set to be equal to or greater than a driving intensity threshold width $\Delta I_{mod, th}$. For example, the driving intensity amplitude $I_{mod, 0}$ of the speckle modulator 200 is set so that a change width $\Delta I_{mod}$ of the driving intensity of the speckle modulator 200 within the effective pulse emission period $t_{pw, eff}$ is equal to or greater than the driving intensity threshold width $\Delta I_{mod, th}$.

Furthermore, in order to enhance the speckle reduction effect, the synchronization controller 240 controls at least the illumination light generator 110 and the speckle modulator 200 in synchronization as follows.

When the effective pulse emission period $t_{pw, eff}$ is a period shorter than ½ of the speckle modulation period $t_{mod}$, the synchronization controller 240 controls the illumination light generator 110 and the speckle modulator 200 so that the effective pulse emission period $t_{pw, eff}$ includes the time at which the change rate of the driving intensity $I_{mod}$ of the speckle modulator reaches a maximum. For example, the synchronization controller 240 controls the illumination light generator 110 and the speckle modulator 200 so that any one of the plurality of illumination pulses includes the time at which the change rate of the driving intensity $I_{mod}$ of the speckle modulator reaches a maximum. Alternatively, the synchronization controller 240 controls the illumination light generator 110 and the speckle modulator 200 so that the center of the effective pulse emission period $t_{pw, eff}$ is the time at which the change rate of the speckle modulator driving intensity $I_{mod}$ reaches a maximum. (Condition D)

Alternatively, when the effective pulse emission period $t_{pw, eff}$ is a period shorter than ½ of the speckle modulation period $t_{mod}$, the synchronization controller 240 controls the illumination light generator 110 and the speckle modulator 200 so that the effective pulse emission period $t_{pw, eff}$ includes neither a maximum value nor a minimum value of the driving intensity $I_{mod}$ of the speckle modulator. (Condition E)

Alternatively, when the effective pulse emission period $t_{pw, eff}$ is a period shorter than ½ of the speckle modulation period $t_{mod}$, the synchronization controller 240 controls the illumination light generator 110 and the speckle modulator 200 so that the effective pulse emission period $t_{pw, eff}$ includes the time at which the effective pulse emission period $t_{pw, eff}$ takes a substantial center value between a maximum value and a minimum value of the driving intensity $I_{mod}$ of the speckle modulator. For example, the synchronization controller 240 controls the illumination light generator 110 and the speckle modulator 200 so that the effective pulse emission period $t_{pw, eff}$ includes the time at which among a plurality of illumination pulses included in one illumination pulse group, any one of the illumination pulses takes a substantial center value between a maximum value and a minimum value of the driving intensity $I_{mod}$ of the speckle modulator 200. Alternatively, the synchronization controller 240 controls the illumination light generator 110 and the speckle modulator 200 so that the center of the effective pulse emission period $t_{pw, eff}$ is the time at which the effective pulse emission period $t_{pw, eff}$ becomes a substantial center value between a maximum value and a minimum value of the driving intensity $I_{mod}$ of the speckle modulator 200. (Condition F)

When the effective pulse emission period $t_{pw, eff}$ is a period equal to or longer than ½ of the speckle modulation period $t_{mod}$, the synchronization controller 240 controls the illumination light generator 110 and the speckle modulator 200 so that the effective pulse emission period $t_{pw, eff}$ includes the time at which the driving intensity $I_{mod}$ of the speckle modulator takes a maximum value and the time at which the driving intensity $I_{mod}$ of the speckle modulator takes a minimum value. (Condition G) There may be one or more further illumination pulses with different time delays synchronized with the speckle modulator 200. When the effective pulse emission period is shorter than ½ of the speckle modulation period $t_{mod}$, it is more preferable to satisfy (Condition D), (Condition E), or (Condition F). For example, when the second illumination pulse group comes exactly half a period after the first illumination pulse group, and if the first illumination pulse group includes the time at which the slope (absolute value) of the driving intensity $I_{mod}$ of the speckle modulator 200 reaches a maximum, the second illumination pulse group also includes the time at which the slope (absolute value) of the driving intensity $I_{mod}$ of the speckle modulator 200 reaches a maximum. When the effective pulse emission period is equal to or longer than ½ of $t_{mod}$, it is more preferable to satisfy (Condition G).

Furthermore, the synchronization controller 240 controls the illumination light generator 110, the speckle modulator 200, and the imager 150 so as to synchronize the pulse generation timing of the illumination light generator 110, the drive timing of the speckle modulator 200, and the imaging timing of the imager 150. The synchronization controller 240 drives the speckle modulator 200 and the illumination light generator 110 with $M_0 \geq 1$. Furthermore, the synchronization controller 240 drives the speckle modulator 200 and the illumination light generator 110 with $t_{mod} \leq 2 M_0 t_{pw,\ eff}$. Alternatively, the synchronization controller 240 drives the speckle modulator 200 and the illumination light generator 110 with $t_{pw,\ eff} < t_{mod} \leq M_0 t_{pw,\ eff}$.

Third Embodiment

In the first embodiment (FIG. 5) and the second embodiment (FIG. 7), the speckle modulator 200 may be composed of at least one of the first light guide characteristic modulator 210, the second light guide characteristic modulator 220, and the wavelength modulator 230, but may be composed of a combination of them.

Figure 9A:
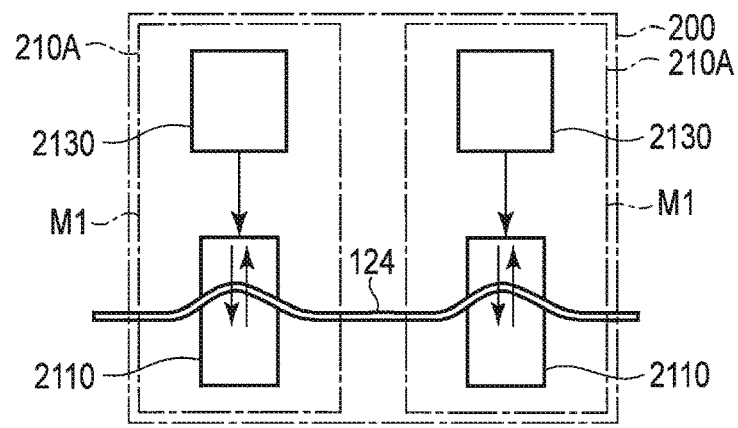
FIG. 9A schematically shows a speckle modulator configured by combining the same two modulators.
Figure 9B:
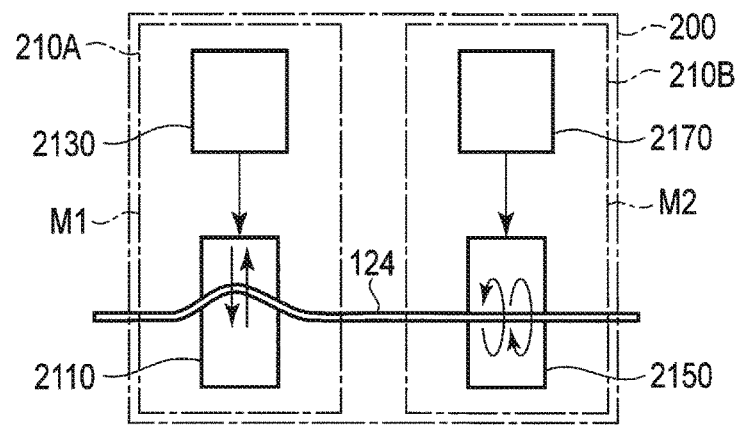
FIG. 9B schematically shows a speckle modulator configured by combining two modulators having different driving mechanisms but the same optical principle.
Figure 9C:
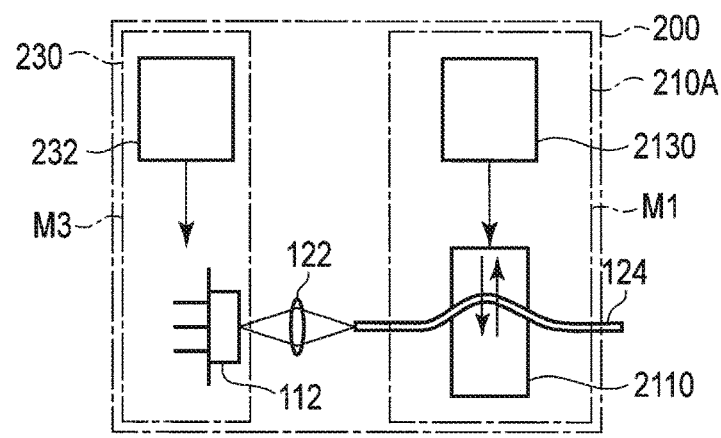
FIG. 9C schematically shows a speckle modulator configured by combining two modulators having different optical principles.

An example of a speckle modulator 200 composed of a combination of two speckle modulators is shown in FIGS. 9A, 9B, and 9C. The speckle reduction effect through the combination of them is as follows.

FIG. 9A schematically shows a speckle modulator 200 composed of a combination of the same two speckle modulators M1 in terms of the driving mechanism and the optical principle. The speckle modulator M1 is configured to apply vibration to a first optical fiber 124. In FIG. 9A, each speckle modulator M1 is typically depicted as the light guide characteristic modulator 210A shown in FIG. 6A.

When the same two speckle modulators M1 are combined, a change in the speckle pattern caused by each of the light guide characteristic modulators 210A is the same, resulting in the following speckle reduction effect $M_{eff,\ total}$ as the overall effect:
when $M_{eff,\ 1}+M_{eff,\ 2}<1$, then $M_{eff,\ total}=M_{eff,\ 1}+M_{eff,\ 2}$
when $M_{eff,\ 1}+M_{eff,\ 2} \geq 1$, $M_{eff,\ total}=1$,
where effective amplitude modulation factor for the respective light guide characteristic modulators 210A are $M_{eff,\ 1}$, and $M_{eff,2}$. This configuration is effective when the speckle reduction effect is insufficient with one speckle modulator M1.

FIG. 9B schematically shows a speckle modulator 200 composed of a combination of two speckle modulators M1 and M2 having different driving mechanisms but the same optical principle. The speckle modulator M1 is as described above. The speckle modulator M2 is configured to apply rotation to the first optical fiber 124. In FIG. 9B, the speckle modulator M2 is typically depicted as the light guide characteristic modulator 210B shown in FIG. 6B.

Also in this case, since the temporal superposition effect of light-dark patterns caused by speckle is used, a configuration is used where optically, speckle modulators M1 and M2 of the same type are combined. Basically, similarly to FIG. 9A, there is an effect in which a resulting pattern is observed in a state where an effective amplitude modulation factor is added. However, light-dark patterns due to speckle caused at the speckle modulators M1 and M2 may change in different ways. For this reason, due to the effect of overlapping various light-dark patterns, the speckle reduction effect in the configuration example of FIG. 9B often becomes stronger (i.e., $M_{eff,\ total}>1$) than in the configuration example of FIG. 9A.

FIG. 9C schematically shows a speckle modulator 200 composed of a combination of two speckle modulators M1 and M3 having different optical principles. The speckle modulator M1 is as described above. The speckle modulator M3 is configured to temporally change the wavelength of laser light. In FIG. 9C, the speckle modulator M3 is depicted as the wavelength modulator 230 shown in FIG. 5.

The two speckle modulators M1 and M3 having different optical principles are connected in series. In this case, due to the difference in optical principle leading to the speckle reduction, the overall speckle reduction effect results as follows. $M_{eff,\ total}=M_{eff,\ 1}+M_{eff,\ 2}$, regardless of the magnitude of $M_{eff,\ 1}+M_{eff,\ 2}$.

In addition, with respect to the configurations shown in FIGS. 9A, 9B, and 9C, the behavior and effect of the synchronization controller 240, etc. are the same as those of the first and second embodiments.

Fourth Embodiment

FIG. 10 schematically shows the overall configuration of the illuminating device according to the fourth embodiment. In FIG. 10, members denoted by the same reference numerals as those shown in FIGS. 5 and 7 are the same members, and detailed descriptions thereof are omitted.

An illuminating device 102B according to the present embodiment includes the illumination light generator 110, a light guide optical system 120B configured to guide laser light emitted from the illumination light generator 110, and a radiating optical system 140B configured to apply laser light guided by the light guide optical system 120B.

The light guide optical system 120B includes a collimating lens 122B configured to collimate a light beam emitted from the illumination light generator 110, and a coupling lens 124B configured to couple the light beam collimated by the collimating lens 122B to the radiating optical system 140B. The collimating lens 122B and the coupling lens 124B are schematically illustrated as a single lens in FIG. 10, but may actually be composed of either one or a plurality of lenses.

The illuminating device 102B also includes the speckle modulator 200, the synchronization controller 240, and a pulse width modulation light controller 250. The speckle modulator 200 includes a light guide characteristic modulator 220 and the wavelength modulator 230. The light guide characteristic modulator 220 is disposed on the optical path of a collimated light beam between the collimating lens 122B and the coupling lens 124B.

Details of the speckle modulator 200, the light guide characteristic modulator 220, the wavelength modulator 230, and the synchronization controller 240 are as described in the first embodiment, and details of the pulse width modulation light controller 250 are as described in the second embodiment.

In the illuminating device 102B including no imager, it is possible for an observer to obtain the same speckle reduction effect as in the first embodiment to the third embodiment by considering, with respect to the change width of the driving intensity of the speckle modulator 200, a change width of the driving intensity of the speckle modulator 200 within a time period considered to be a response time with respect to a change in an image of the living body (or considered to be approximately 33 msec when the living body is a human being).

Fifth Embodiment

FIG. 11 schematically shows the overall configuration of a microscope system including an imaging system according to the fifth embodiment. In FIG. 11, members denoted by the same reference numerals as those shown in FIGS. 5 and 7 are the same members, and detailed descriptions thereof are omitted.

An imaging system 100C according to the present embodiment includes an illuminating device 102C configured to illuminate an observation object 190, and an imaging device 104.

The illuminating device 102C includes the illumination light generator 110, a light guide optical system 120C configured to guide laser light emitted from the illumination light generator 110, and an illumination optical system 400 configured to apply the laser light guided by the light guide optical system 120C.

The light guide optical system 120C includes an optical fiber 126C configured to guide laser light, a collimating lens 122C configured to collimate a light beam emitted from the illumination light generator 110, and a fiber coupling lens 124C configured to couple the light beam collimated by the collimating lens 122C to the optical fiber 126C. The collimating lens 122C and the fiber coupling lens 124C are schematically depicted as one lens in FIG. 11, but may actually be composed of one lens or may be composed of a plurality of lenses.

The illumination optical system 400 includes a collimating optical system 410 configured to collimate a light beam emitted from the optical fiber 126C; a beam splitter 420 configured to split the light beam collimated by the collimating optical system 410 into two light beams; a first mirror 430A configured to reflect one light beam split by the beam splitter 420; a first radiating optical system 440A configured to apply the light beam reflected by the first mirror 430A toward an observation object 190 placed on a sample stage 450 from below; a second mirror 430B configured to reflect the other light beam split by the beam splitter 420; and a second radiating optical system 440B configured to apply the light beam reflected by the second mirror 430B toward the observation object 190 obliquely from above.

The illuminating device 102C also includes the speckle modulator 200, the synchronization controller 240, and the pulse width modulation light controller 250. The speckle modulator 200 includes the first light guide characteristic modulator 210, the second light guide characteristic modulator 220, and the wavelength modulator 230. The second light guide characteristic modulator 220 is disposed on the optical path of a collimated light beam between the collimating lens 122C and the fiber coupling lens 124C. The first light guide characteristic modulator 210 is disposed in a middle part of the optical fiber 126C.

Details of the speckle modulator 200, the first light guide characteristic modulator 210, the second light guide characteristic modulator 220, the wavelength modulator 230, and the synchronization controller 240 are as described in the first embodiment, and details of the pulse width modulation light controller 250 are as described in the second embodiment.

The imaging system 100C also includes an objective optical system 460 disposed so as to face the sample stage 450, a barrel 470 supporting the objective optical system 460, and an eyepiece and an imaging optical system 480 attached to the barrel 470.

The laser light emitted from the light guide optical system 120C is split into two light beams by the beam splitter 420 through the collimating optical system 410. One light beam is reflected by the first mirror 430A and applied toward an observation object 190 through the first radiating optical system 440A from below. In addition, the other light beam is reflected by the second mirror 430B and applied to the observation object 190 obliquely from above through the second radiating optical system 440B.

The light applied to the observation object 190 is reflected, diffracted, scattered, etc. by the observation object 190. A part of the light reflected, diffracted, scattered, etc. by the observation object 190 enters the objective optical system 460. The light that has entered the objective optical system 460 forms an image on the light receiving surface of an imager 150 through, for example, the eyepiece and the imaging optical system 480, and image information on the observation object 190 is acquired by the imager 150. The image information acquired by the imager 150 is displayed on the display 170 after being subjected to image processing by the image processing circuit 160. Alternatively, the light that has entered the objective optical system 460 forms an image on the retina of the observer through the eyepiece and the imaging optical system 480, and an image of the observation object 190 is observed by the observer.

In a microscope system including the imaging system 100C according to the present embodiment, the behavior and effect related to speckle reduction are the same as those obtained in the first to the fourth embodiments.

SUMMARY

Summarizing the above, this specification discloses illuminating devices and imaging systems listed below. In other words, the embodiments described above can be generalized as described below.

[1] An illuminating device comprising:
an illumination light generator configured to generate illumination pulses of coherent light, and
a speckle modulator configured to modulate speckle caused by the coherent light,
the illumination pulse generator being configured to repeatedly generate a single illumination pulse group including a plurality of illumination pulses as a repetitive illumination pulse group.

[2] The illuminating device according to [1], wherein when a time period from the lighting time of a first illumination pulse to the extinction time of a last illumination pulse, in the single illumination pulse group, is regarded as an effective pulse emission period ($t_{pw,\ eff}$), the effective pulse emission period is equal to or longer than twice a net pulse emission period of a plurality of illumination pulses included in the single illumination pulse group.

[3] The illuminating device according to [1], wherein the number of the plurality of illumination pulses included in the single illumination pulse group is three or more.

[4] The illuminating device according to any one of [1] to [3], further comprising: a synchronization controller configured to control the illumination pulse generator and the speckle modulator so as to synchronize pulse generation timing of the illumination pulse generator and drive timing of the speckle modulator.

[5] The illuminating device according to any one of [1], [3], and [4], further comprising:

a synchronization controller configured to control the illumination pulse generator and the speckle modulator so as to synchronize pulse generation timing of the illumination pulse generator and drive timing of the speckle modulator, wherein the synchronization controller is configured to control the speckle modulator so as to operate at least during an effective pulse emission period ($t_{pw, \, eff}$), where effective pulse emission period ($t_{pw, \, eff}$) is a time period from the lighting time of a first illumination pulse to the extinction time of a last illumination pulse, in the single illumination pulse group.

[6] The illuminating device according to any one of [1] to [5], wherein the speckle modulator is configured to periodically change a driving intensity ($I_{mod}$) of the speckle modulator, and a driving intensity amplitude ($\Delta I_{mod, \, 0}$) of the speckle modulator is set to be equal to or greater than a driving intensity threshold width ($\Delta I_{mod, \, th}$), where the driving intensity threshold width ($\Delta I_{mod, \, th}$) is a change width ($\Delta I_{mod}$) of a driving intensity of the speckle modulator at which a reduction in speckle is saturated with respect to a change in the driving intensity of the speckle modulator.

[7] The illuminating device according to [6] depending on [2] or [5], wherein a driving intensity amplitude ($I_{mod, \, 0}$) of the speckle modulator is set so that a change width ($\Delta I_{mod}$) of the driving intensity of the speckle modulator during the effective pulse emission period ($t_{pw, \, eff}$) becomes a value equal to or greater than a driving intensity threshold width ($\Delta I_{mod, \, th}$).

[8] The illuminating device according to [2] or [5], further comprising: a pulse width modulation light controller configured to control an effective illumination light quantity by controlling a pulse width of the plurality of illumination pulses during the effective pulse emission period ($t_{pw, \, eff}$), wherein the pulse width modulation light controller comprises a multi-pulse division type pulse-width modulation light controller configured to divide a pulse emission period ($t_{pw}$) corresponding to a desired light control quantity into a plurality of pulse emission periods ($t_{pw, \, ill, \, 1}, \ldots, t_{pw, \, ill, \, n}$, and n is a natural number of 2 or more).

[9] The illuminating device according to [5], wherein the speckle modulator is configured to periodically change a driving intensity ($I_{mod}$) of the speckle modulator, and the synchronization controller is configured to control the illumination pulse generator and the speckle modulator so that the effective pulse emission period ($t_{pw, \, eff}$) includes the time at which a change rate of the driving intensity ($I_{mod}$) of the speckle modulator reaches a maximum, when the effective pulse emission period ($t_{pw, \, eff}$) is a period shorter than ½ of a speckle modulation period ($t_{mod}$).

[10] The illuminating device according to [9], wherein the synchronization controller is configured to control the illumination pulse generator and the speckle modulator so that any one of the plurality of illumination pulses includes the time at which the change rate of the driving intensity ($I_{mod}$) of the speckle modulator reaches a maximum.

[11] The illuminating device according to [9], wherein the synchronization controller is configured to control the illumination pulse generator and the speckle modulator so that a center of the effective pulse emission period ($t_{pw, \, eff}$) is the time at which the change rate of the driving intensity ($I_{mod}$) of the speckle modulator substantially reaches a maximum.

[12] The illuminating device according to [5], wherein the speckle modulator is configured to periodically change a driving intensity ($I_{mod}$) of the speckle modulator, and the synchronization controller is configured to control the illumination pulse generator and the speckle modulator so that the effective pulse emission period ($t_{pw, \, eff}$) includes neither a maximum value nor a minimum value of the driving intensity ($I_{mod}$) of the speckle modulator, when the effective pulse emission period ($t_{pw, \, eff}$) is a period shorter than ½ of a speckle modulation period ($t_{mod}$).

[13] The illuminating device according to [5], wherein the speckle modulator is configured to periodically change a driving intensity ($I_{mod}$) of the speckle modulator, and the synchronization controller is configured to control the illumination pulse generator and the speckle modulator so that the effective pulse emission period ($t_{pw, \, eff}$) includes the time at which a driving intensity ($I_{mod}$) of the speckle modulator takes a substantial center value between a maximum value and a minimum value of the driving intensity ($I_{mod}$) of the speckle modulator, when the effective pulse emission period ($t_{pw, \, eff}$) is a period shorter than ½ of a speckle modulation period ($t_{mod}$).

[14] The illuminating device according to [13], wherein the synchronization controller is configured to control the illumination pulse generator and the speckle modulator so that the effective pulse emission period ($t_{pw, \, eff}$) includes the time at which any one of the plurality of illumination pulses takes a substantial center value between a maximum value and a minimum value of the driving intensity ($I_{mod}$) of the speckle modulator.

[15] The illuminating device according to [13], wherein the synchronization controller is configured to control the illumination pulse generator and the speckle modulator so that a center of the effective pulse emission period ($t_{pw, \, eff}$) is the time at which the driving intensity ($I_{mod}$) of the speckle modulator takes a substantial center value between a maximum value and a minimum value of the driving intensity ($I_{mod}$) of the speckle modulator.

[16] The illuminating device according to [5], wherein the synchronization controller is configured to control the illumination pulse generator and the speckle modulator so that the effective pulse emission period ($t_{pw, \, eff}$) includes the time at which a driving intensity ($I_{mod}$) of the speckle modulator takes a maximum value and the time at which the driving intensity ($I_{mod}$) of the speckle modulator takes a minimum value, when the effective pulse emission period ($t_{pw, \, eff}$) is a period equal to or longer than ½ of a speckle modulation period ($t_{mod}$).

[17] The illuminating device according to any one of [1] to [5], wherein the speckle modulator includes a phase modulator configured to temporally change a phase of the coherent light.

[18] The illuminating device according to [17], wherein the phase modulator includes a light guide variation device configured to apply a mechanical change to a light guide included in a light guide optical system configured to guide the coherent light.

[19] The illuminating device according to [17], wherein the phase modulator includes a concavo-convex plate with protrusions and recesses greater than ¹/₁₀ a wavelength of the coherent light.

[20] The illuminating device according to [17], wherein the phase modulator comprises a refractive index modulator configured to temporally change a refractive index of a light guide optical system configured to guide the coherent light.

[21] The illuminating device according to [20], wherein the refractive index modulator includes at least one of an electro-optic element and an acousto-optic element.

[22] The illuminating device according to [18], wherein the light guide optical system includes an optical fiber, and a driving intensity amplitude ($I_{mod,\ 0}$) of the speckle modulator is 5Φc or more in terms of displacement of vibration of the optical fiber caused by the light guide variation device, where Φc is a core diameter of the optical fiber.

[23] The illuminating device according to [18], wherein the light guide optical system includes an optical fiber, and a driving intensity amplitude ($I_{mod,\ 0}$) of the speckle modulator is 10° or more in terms of an angle at which the optical fiber is twisted.

[24] The illuminating device according to [20], wherein a driving intensity amplitude ($I_{mod,\ 0}$) of the speckle modulator is $\Delta n/n \geq \lambda c/Lm$ in terms of a change in refractive index of the refractive index modulator, where Lm is a length of the refractive index modulator in a light guide direction, $\Delta n/n$ is a change in refractive index, and $\lambda c$ is a center wavelength of a spectrum of an illumination pulse.

[25] An imaging system including: the illuminating device according to any one of [5] to [16], and an imager configured to perform imaging within a predetermined exposure period ($t_{pw,\ exp}$), the synchronization controller being configured to control the illumination pulse generator, the speckle modulator, and the imager so as to synchronize pulse generation timing of the illumination pulse generator, drive timing of the speckle modulator, and imaging timing of the imager.

[26] The imaging system according to [25], wherein the synchronization controller is configured to control the illumination pulse generator so as to generate the illumination pulses within an exposure period ($t_{pw,\ exp}$) of the imager.

[27] The imaging system according to [25] or [26], further comprising:
a pulse width modulation light controller configured to control an effective illumination light quantity by controlling a pulse width of the plurality of illumination pulses during an effective pulse emission period ($t_{pw,\ eff}$), wherein
the pulse width modulation light controller comprises a multi-pulse division type pulse-width modulation light controller configured to divide a pulse emission period ($t_{pw}$) corresponding to a desired light control quantity into a plurality of pulse emission periods ($t_{pw,\ ill,\ 1}, \ldots, t_{pw,\ ill,\ n}$, and n is a natural number of 2 or more).

[28] The imaging system according to [25] or [26], wherein the speckle modulator is configured to periodically change a driving intensity ($I_{mod}$) of the speckle modulator, and the synchronization controller is configured to control the illumination pulse generator and the speckle modulator so that the effective pulse emission period ($t_{pw,\ eff}$) includes the time at which a change rate of the driving intensity ($I_{mod}$) of the speckle modulator reaches a maximum.

[29] The imaging system according to [28], wherein the synchronization controller is configured to control the illumination pulse generator and the speckle modulator so that any one of the plurality of illumination pulses includes the time at which the change rate of the speckle modulator ($I_{mod}$) of the speckle modulator reaches a maximum.

[30] The imaging system according to [28], wherein the synchronization controller is configured to control the illumination pulse generator and the speckle modulator so that a center of the effective pulse emission period ($t_{pw,\ eff}$) is the time at which the change rate of the driving intensity ($I_{mod}$) of the speckle modulator substantially reaches a maximum.

[31] The imaging system according to [25] or [26], wherein the speckle modulator is configured to periodically change a driving intensity ($I_{mod}$) of the speckle modulator, and the synchronization controller is configured to control the illumination pulse generator and the speckle modulator so that the effective pulse emission period ($t_{pw,\ eff}$) includes neither a maximum value nor a minimum value of the driving intensity ($I_{mod}$) of the speckle modulator, when the effective pulse emission period ($t_{pw,\ eff}$) is a period shorter than ½ of a speckle modulation period ($t_{mod}$).

[32] The imaging system according to [25] or [26], wherein the speckle modulator is configured to periodically change a driving intensity ($I_{mod}$) of the speckle modulator, and the synchronization controller is configured to control the illumination pulse generator and the speckle modulator so that the effective pulse emission period ($t_{pw,\ eff}$) includes the time at which a driving intensity ($I_{mod}$) of the speckle modulator takes a substantial center value between a maximum value and a minimum value of the driving intensity ($I_{mod}$) of the speckle modulator, when the effective pulse emission period ($t_{pw,\ eff}$) is a period shorter than ½ of a speckle modulation period ($t_{mod}$).

[33] The imaging system according to [32], wherein the synchronization controller is configured to control the illumination pulse generator and the speckle modulator so that the effective pulse emission period ($t_{pw,\ eff}$) includes the time at which any one of the plurality of illumination pulses takes a substantial center value between a maximum value and a minimum value of the driving intensity ($I_{mod}$) of the speckle modulator.

[34] The imaging system according to [32], wherein the synchronization controller is configured to control the illumination pulse generator and the speckle modulator so that a center of the effective pulse emission period ($t_{pw,\ eff}$) is the time at which the driving intensity ($I_{mod}$) of the speckle modulator takes a substantial center value between a maximum value and a minimum value of the driving intensity ($I_{mod}$) of the speckle modulator.

[35] The imaging system according to [25] or [26], wherein the synchronization controller is configured to control the illumination pulse generator and the speckle modulator so that the effective pulse emission period ($t_{pw,\ eff}$) includes the time at which a driving intensity ($I_{mod}$) of the speckle modulator takes a maximum value and the time at which the driving intensity ($I_{mod}$) of the speckle modulator takes a minimum value, when the effective pulse emission period ($t_{pw,\ eff}$) is a period equal to or longer than ½ of a speckle modulation period ($t_{mod}$).

[36] The imaging system according to [25], wherein
the synchronization controller is configured to control the illumination pulse generator, the speckle modulator, and the imager so as to synchronize pulse generation timing of the illumination pulse generator, drive timing of the speckle modulator, and imaging timing of the imager, and
the synchronization controller is configured to drive the speckle modulator and the illumination pulse generator with $M_0 \geq 1$ and with $t_{mod} \leq 2M_0 t_{pw,\ eff}$, where $M_0 = I_{mod,\ 0}/\Delta I_{mod,\ th}$, $I_{mod,\ 0}$ is a driving intensity amplitude of the speckle modulator; $\Delta I_{mod,\ th}$ is a driving intensity threshold width that is a change width of a driving intensity of the speckle modulator at which a reduction in speckle is saturated with respect to a change in the driving intensity of the speckle modulator; $t_{pw,\ eff}$ is the effective pulse emission period of the illumination pulses generated by the illumination pulse generator; and $t_{mod}$ is a modulation period when the speckle modulator is periodically driven.

[37] The imaging system according to [25], wherein
the synchronization controller is configured to control the illumination pulse generator, the speckle modulator, and the imager so as to synchronize pulse generation timing of the illumination pulse generator, drive timing of the speckle modulator, and imaging timing of the imager, and
the synchronization controller is configured to drive the speckle modulator and the illumination pulse generator with $M_0 \geq 1$ and with $t_{pw,\ eff} \leq t_{mod} \leq M_0 t_{pw,\ eff}$, where $M_0 = I_{mod,\ 0}/\Delta I_{mod,\ th}$, $I_{mod,\ 0}$ is a driving intensity amplitude of the speckle modulator; $\Delta I_{mod,\ th}$ is a driving intensity threshold width that is a change width of a driving intensity of the speckle modulator at which a reduction in speckle is saturated with respect to a change in the driving intensity of the speckle modulator; $t_{pw,\ eff}$ is the effective pulse emission period of the illumination pulses generated by the illumination pulse generator; and $t_{mod}$ is a modulation period when the speckle modulator is periodically driven.

[38] The imaging system according to any one of [25] to [37], wherein the speckle modulator includes a phase modulator configured to temporally change a phase of the coherent light.

[39] The imaging system according to [38], wherein the phase modulator includes a light guide variation device configured to apply a mechanical change to a light guide included in a light guide optical system configured to guide the coherent light.

[40] The imaging system according to [38], wherein the phase modulator includes a concavo-convex plate with protrusions and recesses greater than 1/10 a wavelength of the coherent light.

[41] The imaging system according to [38], wherein the phase modulator comprises a refractive index modulator configured to temporally change a refractive index of a light guide optical system configured to guide the coherent light.

[42] The imaging system according to [41], wherein the refractive index modulator includes at least one of an electro-optic element and an acousto-optic element.

[43] The imaging system according to [39], wherein the light guide optical system includes an optical fiber, and a driving intensity amplitude ($I_{mod,\ 0}$) of the speckle modulator is 5Φc or more in terms of displacement of vibration of the optical fiber caused by the light guide variation device, where Φc is a core diameter of the optical fiber.

[44] The imaging system according to [39], wherein the light guide optical system includes an optical fiber, and a driving intensity amplitude ($I_{mod,\ 0}$) of the speckle modulator is 10° or more in terms of an angle at which the optical fiber is twisted.

[45] The imaging system according to [41], wherein a driving intensity amplitude ($I_{mod,\ 0}$) of the speckle modulator is $\Delta n/n \geq \lambda c/Lm$ in terms of a change in refractive index of the refractive index modulator, where Lm is a length of the refractive index modulator in a light guide direction, $\Delta n/n$ is a change in refractive index, and $\lambda c$ is a center wavelength of a spectrum of an illumination pulse.

[46] An endoscope system including the imaging system according to any one of [25] to [45], wherein the imaging system further comprises: an image processing circuit configured to perform image processing on an image imaged by the imager; and an image display configured to display an image that has been subjected to the image processing by the image processing circuit.

[47] A microscope system including the imaging system according to any one of [25] to [45], wherein the imaging system further comprises: an image processing circuit configured to perform image processing on an image imaged by the imager; and an image display configured to display an image that has been subjected to the image processing by the image processing circuit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illuminating device comprising:
   an illumination light generator configured to repeatedly generate a single illumination pulse group including a plurality of illumination pulses of coherent lights; and
   a speckle modulator configured to modulate speckle caused by the coherent lights, and to periodically change a driving intensity of the speckle modulator,
   wherein a driving intensity amplitude width of the driving intensity is configured to be set to be equal to or greater than a driving intensity threshold width, and
   wherein the driving intensity threshold width is set to saturate a reduction of the speckle.

2. The illuminating device according to claim 1,
   wherein the plurality of illumination pulses comprises a first illumination pulse and a second illumination pulse,
   wherein an effective pulse emission period of the plurality of illumination pulses is defined from a lighting time of the first illumination pulse to an extinction time of a last the second illumination pulse,
   wherein a net pulse emission period of the plurality of illumination pulses is defined as emission times of the plurality of illumination pulses without extinction time of the plurality of illumination pulses, and
   wherein the effective pulse emission period is equal to or longer than twice the net pulse emission period.

3. The illuminating device according to claim 2,
   wherein a driving intensity amplitude of the speckle modulator is set to be equal to or greater than the driving intensity threshold width during the effective pulse emission period.

4. The illuminating device according to claim 1,
   wherein the plurality of illumination pulses comprises three or more pulses.

5. The illuminating device according to claim 1, further comprising:
   a synchronization controller configured to control the illumination light generator and the speckle modulator so as to synchronize pulse generation timing of the illumination light generator and drive timing of the speckle modulator.

6. The illuminating device according to claim 5,
   wherein the plurality of illumination pulses comprises a first illumination pulse and a second illumination pulse, and
   wherein the synchronization controller is configured to control the speckle modulator so as to operate at least during an effective pulse emission period of the plurality of illumination pulses, where the effective pulse emission period is defined from a lighting time of the first illumination pulse to an extinction time of the second illumination pulse.

7. The illuminating device according to claim 6, further comprising:
a pulse width modulation light controller configured to control an effective illumination light quantity by controlling a pulse width of the plurality of illumination pulses during the effective pulse emission period,
wherein the pulse width modulation light controller comprises a multi-pulse division type pulse-width modulation light controller configured to divide a pulse emission period corresponding to a desired light control quantity into a plurality of pulse emission periods.

8. The illuminating device according to claim 6,
wherein the synchronization controller is configured to control the illumination light generator and the speckle modulator so that the effective pulse emission period includes the time at which a change rate of the driving intensity of the speckle modulator reaches a maximum, when the effective pulse emission period is a period shorter than ½ of a speckle modulation period.

9. The illuminating device according to claim 6,
wherein the synchronization controller is configured to control the illumination light generator and the speckle modulator so that the effective pulse emission period includes neither a maximum value nor a minimum value of a driving intensity of the speckle modulator, when the effective pulse emission period is a period shorter than ½ of a speckle modulation period.

10. The illuminating device according to claim 6,
wherein the synchronization controller is configured to control the illumination light generator and the speckle modulator so that the effective pulse emission period includes the time at which the driving intensity of the speckle modulator takes a substantial center value between a maximum value and a minimum value of the driving intensity of the speckle modulator, when the effective pulse emission period is a period shorter than ½ of a speckle modulation period.

11. The illuminating device according to claim 1, wherein the speckle modulator comprises a phase modulator configured to temporally change a phase of the coherent lights.

12. The illuminating device according to claim 11,
wherein the phase modulator is configured to apply a mechanical change to an optical fiber configured to guide the coherent lights,
wherein the driving intensity amplitude of the speckle modulator is $5\Phi c$ or more in terms of displacement of vibration of the optical fiber caused by the phase modulator, where $\Phi c$ is a core diameter of the optical fiber, and
wherein the driving intensity amplitude of the speckle modulator is $10°$ or more in terms of an angle at which the optical fiber is twisted.

13. The illuminating device according to claim 11,
wherein the phase modulator comprises a concavo-convex plate with protrusions and recesses greater than $1/10$ a wavelength of the coherent lights.

14. The illuminating device according to claim 11,
wherein the phase modulator is configured to temporally change a refractive index of a light guide optical system configured to guide the coherent lights,
wherein the phase modulator comprises at least one of an electro-optic element and an acousto-optic element, and
wherein the driving intensity amplitude of the speckle modulator is $\Delta n/n \geq \lambda c/Lm$ in terms of a change in refractive index of the phase modulator, where Lm is a length of the phase modulator in a light guide direction, $\Delta n/n$ is a change in refractive index, and $\lambda c$ is a center wavelength of a spectrum of an illumination pulse.

15. An imaging system comprising:
an illumination light generator configured to repeatedly generate a single illumination pulse group including a plurality of illumination pulses of coherent lights;
a speckle modulator configured to modulate speckle caused by the coherent lights, and to periodically change a driving intensity of the speckle modulator,
wherein a driving intensity amplitude width of the driving intensity is configured to be set to be equal to or greater than a driving intensity threshold width, and
wherein the driving intensity threshold width is set to saturate a reduction of the speckle;
an imager configured to perform imaging within a predetermined exposure period; and
a synchronization controller configured to:
control the illumination light generator, the speckle modulator, and the imager so as to synchronize pulse generation timing of the illumination light generator, drive timing of the speckle modulator, and imaging timing of the imager; and
control the illumination light generator so as to generate the plurality of illumination pulses within an exposure period of the imager.

16. The imaging system according to claim 15, further comprising:
a pulse width modulation light controller configured to control an effective illumination light quantity by controlling a pulse width of the plurality of illumination pulses during an effective pulse emission period,
wherein the pulse width modulation light controller comprises a multi-pulse division type pulse-width modulation light controller configured to divide a pulse emission period corresponding to a desired light control quantity into a plurality of pulse emission periods.

17. The imaging system according to claim 16,
wherein the synchronization controller is configured to control the illumination light generator, the speckle modulator, and the imager so as to synchronize the pulse generation timing of the illumination light generator, the drive timing of the speckle modulator, and the imaging timing of the imager, and
wherein:
the synchronization controller is configured to drive the speckle modulator and the illumination light generator with $M_0 \geq 1$ and with $t_{mod} \leq 2M_0 t_{pw, eff}$, or
the synchronization controller is configured to drive the speckle modulator and the illumination light generator with $M_0 \geq 1$ and with $t_{pw, eff} < t_{mod} \leq M_0 t_{pw, eff}$,
where $M_0 = I_{mod, 0}/\Delta I_{mod, th}$, $I_{mod, 0}$ is a driving intensity amplitude of the speckle modulator; $\Delta I_{mod, th}$ is a driving intensity threshold width that is a change width of a driving intensity of the speckle modulator at which a reduction in speckle is saturated with respect to a change in the driving intensity of the speckle modulator; $t_{pw, eff}$ is the effective pulse emission period of the illumination pulses generated by the illumination light generator; and $t_{mod}$ is a modulation period when the speckle modulator is periodically driven.

18. An endoscope system comprising:
the imaging system according to claim 15,
wherein the imaging system further comprises:
- an image processing circuit configured to:
  - perform image processing on an image imaged by the imager; and
  - control an image display to display an image that has been subjected to the image processing.

19. A microscope system comprising:
the imaging system according to claim 15,
wherein the imaging system further comprises:
- an image processing circuit configured to:
  - perform image processing on an image imaged by the imager; and
  - an image display configured to display an image that has been subjected to the image processing by the image processing circuit.

20. An illuminating device comprising:
an illumination light generator configured to repeatedly generate a single illumination pulse group including a plurality of illumination pulses of coherent lights; and
a speckle modulator configured to modulate speckle caused by the coherent lights, and to periodically change a driving intensity of the speckle modulator,
wherein a driving intensity amplitude width of the driving intensity is configured to be set to include a part of a driving intensity threshold width, and
wherein the driving intensity threshold width is set as half or more value relative to a value that is set to saturate the reduction of the speckle.

* * * * *